United States Patent
Shamun et al.

(10) Patent No.: US 11,481,573 B2
(45) Date of Patent: Oct. 25, 2022

(54) METHOD AND SYSTEM OF MODELLING A MENTAL/EMOTIONAL STATE OF A USER

(71) Applicant: Murata Manufacturing Co., Ltd., Nagaokakyo (JP)

(72) Inventors: Ido Shamun, Holon (IL); Nimrod Kramer, Jerusalem (IL); Maayan Yazdi, Jerusalem (IL); Itai Terner, Harish (IL); Tsahi Matsliah, Ramla (IL)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 329 days.

(21) Appl. No.: 16/904,672

(22) Filed: Jun. 18, 2020

(65) Prior Publication Data
US 2020/0320335 A1 Oct. 8, 2020

Related U.S. Application Data

(63) Continuation of application No. PCT/IL2018/051378, filed on Dec. 19, 2018.
(Continued)

(51) Int. Cl.
*G06K 9/62* (2022.01)
*G06F 3/01* (2006.01)
(Continued)

(52) U.S. Cl.
CPC ............. *G06K 9/623* (2013.01); *G06F 3/015* (2013.01); *G06K 9/6218* (2013.01);
(Continued)

(58) Field of Classification Search
CPC .... G06K 9/623; G06K 9/6218; G06K 9/6256; G06F 3/015; G06F 2203/011; G06N 3/08;
(Continued)

(56) References Cited

U.S. PATENT DOCUMENTS 9,269,374 B1 * 2/2016 Conway ................. G06V 40/20
10,135,989 B1 * 11/2018 Indyk ...................... G10L 15/14
(Continued)

OTHER PUBLICATIONS

International Search Report issued for PCT/IL2018/051378, dated Feb. 28, 2019.
(Continued)

*Primary Examiner* — Samir A Ahmed
(74) *Attorney, Agent, or Firm* — ArentFox Schiff LLP

(57) ABSTRACT

A computer-controlled system for providing prediction models for prediction of mental/emotional state of a user. The prediction models are one or more of a first models based on non-physiological data gathered from a first group of users and second models based on physiological data gathered from a second group of users. The prediction model form a set of models. The system receives data of a tested user and associates at least one model of the set of models to the tested user, forming an associated prediction model, based at least on a highest rank of user state predictability of the associated prediction model compared to a rank of user state predictability of other models of the set of models. The associated prediction model is usable to facilitate predicting emotional/mental state of the tested user.

30 Claims, 15 Drawing Sheets

Related U.S. Application Data

(60) Provisional application No. 62/607,945, filed on Dec. 20, 2017.

(51) Int. Cl.
*G06N 3/08* (2006.01)
*G06V 10/75* (2022.01)

(52) U.S. Cl.
CPC .............. *G06K 9/6256* (2013.01); *G06N 3/08* (2013.01); *G06V 10/751* (2022.01); *G06F 2203/011* (2013.01)

(58) Field of Classification Search
CPC ...... G06V 10/751; G16H 50/20; A61B 5/165; A61B 5/7264
See application file for complete search history.

(56) References Cited

U.S. PATENT DOCUMENTS

| | | |
|---|---|---|
| 2016/0007899 A1 | 1/2016 | Durkee et al. |
| 2016/0302711 A1 | 10/2016 | Frank et al. |
| 2017/0076740 A1* | 3/2017 | Feast ..................... H04L 67/535 |
| 2017/0095192 A1 | 4/2017 | Sadowsky et al. |

OTHER PUBLICATIONS

Written Opinion of the International Searching Authority issued for PCT/IL2018/051378, dated Feb. 28, 2019.

* cited by examiner

| Physiological Data ||
|---|---|
| Device ID | 1 |
| User ID | 280 |
| Organization ID | 73 |
| Sample | 160b -1<br>160b-2<br>Etc. ... |
| Other metadata | .... |

160a

| Sample ||
|---|---|
| timestamp | 2017-08-23 00:07:14.010 UTC |
| dls | 0.454 |
| spo2 | 0 |
| hr | 155 |
| Pulse amplitude | 5 |
| Blood velocity | 4853.02 |
| hrv | 101 |
| Motion value | 1212.4 |
| Skin temperature | 29.75 |
| flow1 | 545 |
| flow2 | 341 |
| flow3 | 154 |
| flow4 | 209 |
| Blood perfusion | 294 |
| ppg ir | -182.484 |
| ppg red | -63.15 |
| acc1 | -5499 |
| acc2 | -4049 |
| acc3 | 14506 |
| Other data | ... |

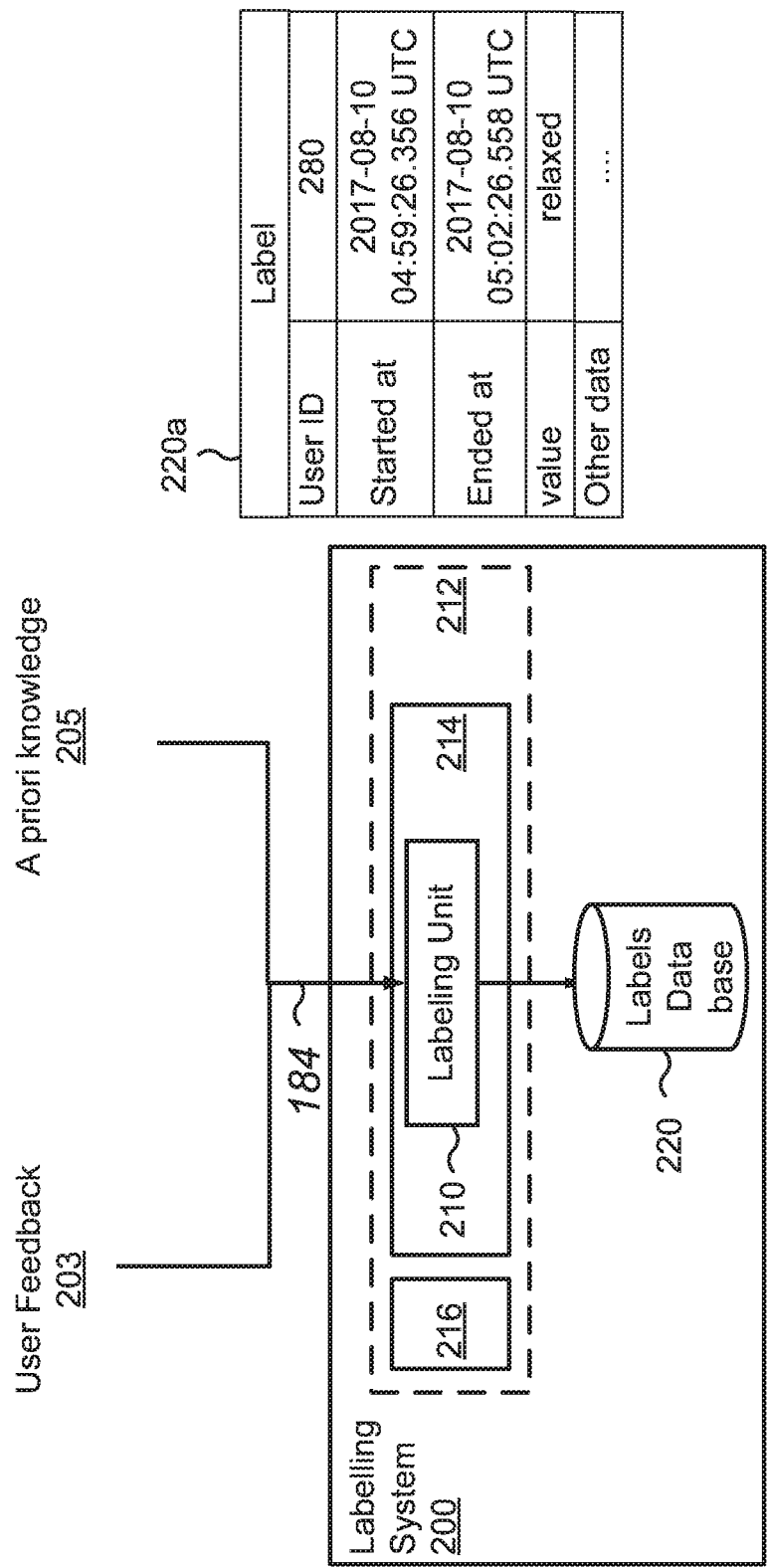

METHOD AND SYSTEM OF MODELLING A MENTAL/EMOTIONAL STATE OF A USER

CROSS REFERENCE TO RELATED APPLICATIONS

The present application is a continuation of PCT/IL2018/051378 filed Dec. 19, 2018, which claims priority to U.S. Provisional Patent Application No. 62/607,945, filed Dec. 20, 2017, the entire contents of each of which are incorporated herein by reference.

TECHNICAL FIELD

The presently disclosed subject matter relates to computer systems and methods for predicting emotional and/or mental states of a user.

BACKGROUND

Currently, the medical and healthcare domain has evolved in such a way that more technologies and methods of monitoring the human body are available than ever before. In particular, monitoring systems of physiological and vital signs have become accurate and reliable, thus offering solid ground for health decisions and treatments. For example, off-the-shelf products, like smartwatches and fitness bracelets, offer users an accurate, ongoing measurement of their body. This kind of monitoring is enabling a wide range of solutions that strive to improve one's medical wellbeing and fitness conditions.

In parallel, it is also known in the academic literature, and as a matter of public knowledge, that there is a strong correlation between the physiological condition of the body and its mental and/or emotional condition. However, the most common ways to measure and monitor emotional and/or mental states are subjective, and are dependent on the individual's perspectives and experiences. The most common methods are clinical sessions with professionals (e.g., therapists, psychologists, etc.), questionnaires, and other methods. Current methods involve substantial problems in terms of consistency of information and reliability, especially when measuring and/or monitoring emotional and/or mental states over time. Another family of solutions aims at more accurate and reliable detection results (such as placing the fingers in a medical device and calculating a current mental state). However, such solutions provide a one-time measurement of a very specific moment in time (usually while visiting a clinic).

In addition, it is widely acknowledged that the body's reaction to triggering of a mental state differs from one individual to another in such way that there is an immense variance. Such variance poses a challenge for upcoming technologies in providing accurate and reliable emotional and/or mental state monitoring, as every user has a different physiological reaction.

The effect of stress of the modern world on human health (e.g., stress-related illnesses, increased risk of heart attacks, strokes, etc.), economies (e.g., from a national level through corporates and individuals) and workers' safety (e.g., mainly stress-related accidents) is widely discussed and researched. Thus, modelling a human emotional state and/or mental state may be used to predict a stressful state and/or stress of the human body and/or the reaction of the human body to stress.

SUMMARY OF THE INVENTION

In accordance with an aspect of the invention, there is presented a computer-controlled system, comprising a processing circuitry, the processing circuitry configured to (a) provide at least one prediction model for prediction of at least one of a mental state of a user and an emotional state of the user, wherein the at least one prediction model is at least one of at least one first model based on non-physiological data gathered from a first group of users and at least one second model based on physiological data gathered from a second group of users, with the at least one prediction model forming a set of models. Moreover, the processing circuitry (b) receives data of a tested user, and (c) associates at least one model of the set of models to the tested user, forming an associated prediction model, based at least on a highest rank of user state predictability of the associated prediction model compared to a rank of user state predictability of other models of the set of models. According to the exemplary aspect, the associated prediction model is usable to facilitate predicting at least one of a mental state of the tested user and an emotional state of the tested user.

In addition to the above features, the system according to the exemplary aspect can include one or more of features (i) to (xii) listed below, in any desired combination or permutation:

(i) the received data of a tested user comprises physiological data.
(ii) the received data of a tested user further comprises label data corresponding to at least a portion of the physiological data.
(iii) the highest rank of user state predictability of the associated at least one model and the rank of user state predictability of other models are determined at least based on the physiological data gathered from the first group of users and from the second group of users.
(iv) the highest rank of user state predictability of the associated prediction model and the rank of user state predictability of other models being indicative of at least one of one of the mental state of the tested user and the emotional state of the tested user.
(v) the association of the at least one model of the set of models to the tested user being based at least partly on at least one association model.
(vi) the processing circuitry further configured to:
  d. dynamically repeat said step (c) in response to determining that a rank of user state predictability of another prediction model is higher than a rank of user state predictability of the associated prediction model,
  e. setting the other prediction model to form the associated prediction model.
(vii) the determining that the rank of user state predictability of the modified model is higher than the rank of user state predictability of the previously associated model is based at least partly on monitoring of physiological data of the tested user.
(viii) the processing circuitry being further configured to:
  f. generate an individual model; and
  g. associate the individual model to the tested user, based at least on a highest rank of user state predictability of the individual model compared to a rank of user state predictability of the associated prediction model.
(ix) the generating the individual model, and the associating of the individual model, are based at least on the rank of user state predictability of the models of the set of models not meeting a threshold.
(x) the threshold is 65 percent.

(xi) the processing circuitry being further configured to:
  h. predict the at least one of the mental state of the tested user and the emotional state of the tested user, using the associated model.
(xii) the data of the tested user comprises labels indicative of at least one of a mental state of the user and an emotional state of the tested user, corresponding to at least a portion of the data of the tested user, wherein the associating being based at least partly on the labels.

In accordance with another aspect of the exemplary aspect, there is presented a computer-controlled system, comprising a processing circuitry, the processing circuitry configured to:
  a. receive physiological data of at least one user; and
  b. generate at least one prediction model, based at least on the physiological data, wherein the generated at least one prediction model is usable to facilitate predicting at least one of a mental state of the tested user and an emotional state of the tested user.

In addition to the above features, the system according to this aspect of the presently disclosed subject matter can include one or more of features (xiii) to (xix) listed below, in any desired combination or permutation:
  (xiii) the step (a) comprises receiving labels indicative of at least one of a mental state of the user and an emotional state of the user, corresponding to at least a portion of the physiological data of the at least one user, wherein the generating of the at least one prediction model being at least partly on the labels.
  (xiv) the generating of the at least one prediction model comprises training the at least one prediction model according to a neural network training method.
  (xv) the generating of the at least one prediction model utilizes at least one association model.
  (xvi) the physiological data of the at least one user comprises physiological data of a plurality of users, wherein the physiological data of the plurality of users share similarities, wherein the generation of the at least one model for prediction being based at least partly on the similarities.
  (xvii) the similarities comprise similarities in physiological patterns.
  (xviii) the processing circuitry being further configured to:
    c. re-train the at least one prediction model, the retraining comprising repeating said steps (b) in response to receiving updated physiological data of at least one user.
  (xix) the generation of the at least one prediction model comprises:
    i. training a first portion of the physiological data;
    ii. assessing the accuracy of the at least one prediction model based on a second untrained portion of the physiological data;
    iii. setting a rank of the at least one prediction model based on the assessment; and
    iv. storing the at least one prediction model in the models database based on the assessment.

In accordance with another exemplary aspect of the invention, there is presented a computer-controlled system, comprising a processing circuitry that is configured to:
  a. receive at least one of non-physiological data of a first group of users and physiological data of a second group of users, the at least one of non-physiological data and physiological data constituting user input data; and
  b. generate at least one association model, based at least on the user input data, wherein the generated at least one association model is usable to facilitate at least one of: training of prediction models for prediction of at least one of a mental state of a user and an emotional state of the user, associating users to prediction models.

In addition to the above features, the system according to this exemplary aspect can include one or more of features (xx) to (xxv) listed below, in any desired combination or permutation:
  (xx) the training of the association models is based at least on second physiological data.
  (xxi) the at least one association model comprising at least one non-physiological association model, wherein the generating of the at least one association model is based on at least non-physiological data of the user input data.
  (xxii) the at least one association model comprising at least one physiological association model, wherein the generating of the at least one association model is based on at least physiological data of the user input data.
  (xxiii) the generating of the at least one association model comprises training the at least one association model according to a neural network training method.
  (xxiv) the user input data comprises user input data of a plurality of users, wherein the user input data of the plurality of users share similarities, wherein the generation of the at least one association model being based at least partly on the similarities.
  (xxv) the processing circuitry further being configured to:
    c. re-train the at least one association model, the retraining comprising repeating said steps (b) in response to receiving at least one of updated non-physiological data of a first group of users and updated physiological data of a second group of users, the at least one of non-physiological data and physiological data constituting updated user input data.

In addition to the above features, the system according to any of the above exemplary aspects can include feature (xxvi) listed below, in any desired combination or permutation which is technically possible:
  (xxvi) the physiological data comprise at least one of heart rate, skin conductivity, body temperature, pulse, blood perfusion and blood flow.

According to another exemplary aspect, there is presented the method performed by the system of any of the above aspects.

According to another exemplary aspect, there is presented a non-transitory program storage device readable by machine, tangibly embodying a program of instructions executable by the machine to perform any of the above methods.

The computerized methods, and the non-transitory computer readable storage media disclosed herein according to various aspects, can optionally further comprise one or more of features (i) to (xxvi) listed above, in any possible combination or permutation as would be appreciated to one skilled in the art.

In accordance with an exemplary aspect, there is provided a computer controlled system for modelling a mental state of a tested user comprising, by a processor: a physiological data gathering module configured to gather physiological data of a user according to one or more physiological measurements of the user acquired over a time frame; a non-physiological data gathering module configured to gather non-physiological data of a user; a labelling module configured to provide one or more labels indicative of the user's mental state at a time mark in the time frame based on at least one of user non-physiological data and the physiological data of the user; and a modelling module configured to generate at least one of a first model based on non-physiological data gathered from a first group of users, a second model based on the one or more labels and the physiological data gathered from a second group of users and a third model including an individual model configured to predict a mental state of an individual user. Moreover, each one of the first model, the second model and the third model is associated with a rank of a user mental state predictability configured to facilitate prediction of the mental state of the tested user.

In accordance with an exemplary embodiment, there is further provided a system, wherein the rank of a user mental state predictability is determined according to physiological data of the tested user which gathered over the time frame.

In accordance with an exemplary embodiment, there is yet further provided a system, wherein, for a model of the first, second and third models, the modelling module is configured to predict the mental state of the tested user based on at least a portion of the gathered data and compare the predicted mental state with a corresponding mental state as indicated by a label of the labels and determine the rank associated with the model according to one or more performance metrics of the comparison.

In accordance with an exemplary embodiment, there is further provided a system, wherein the model comprises one of the first second of third models.

In accordance with an exemplary embodiment, there is further provided a system, wherein the modelling module is configured to associate to the tested user the model of the first, second and third models having the highest rank of the user mental state predictability.

In accordance with an exemplary embodiment, there is yet further provided a system, wherein the first model and the second model are arranged in one or more clusters, a cluster of the one or more clusters comprise at least two users having at least one of common physiological data and common non-physiological data.

In accordance with an exemplary embodiment, there is yet further provided a system, wherein the processor comprises: a prediction module configured to predict the mental state of the user based on at least one of the first model the second model and the third model without utilizing the mental state data as indicated by the labels.

In accordance with an exemplary embodiment, there is yet further provided a system, wherein the prediction module is configured to predict the mental state of the user by using the first model to the tested user non-physiological data.

In accordance with an exemplary embodiment, there is yet further provided a system, wherein the prediction module is configured to predict the mental state of the user by using the second model to the user physiological data.

In accordance with an exemplary embodiment, there is yet further provided a system, wherein the prediction module is configured to predict the mental state of the user by using the third model to the physiological data of the user.

In accordance with an exemplary embodiment, there is yet further provided a system, wherein the prediction module is configured to receive at least a portion of the physiological data of the tested user and predict the mental state of the user based on at least one of the first model the second model and the third model.

In accordance with an exemplary embodiment, there is yet further provided a system comprising an analytic unit configured to receive from the prediction module data related to a predicted mental state of one or more users and to generate aggregated business insights of the one or more users.

In accordance with an exemplary embodiment, there is yet further provided a system, wherein the modelling module comprises a pre-processing module configured to receive the one or more labels from the labelling module and the physiological data to generate a dataset based on the physiological data and the one or more labels.

In accordance with an exemplary embodiment, there is yet further provided a system, wherein the modelling module comprises a clustering module to instruct the pre-processing module to generate the dataset based on at least one of a selected physiological data of the physiological data and a selected label of the one or more the labels.

In accordance with an exemplary embodiment, there is yet further provided a system wherein the modelling module comprises a training module configured to receive the dataset from the pre-processing module, to generate the second model by training the dataset according to a training task from the clustering module.

In accordance with an exemplary embodiment, there is yet further provided a system, wherein the training model comprises one or more graphic processing units (GPU) to train the dataset and the third model according to a neural network training method.

In accordance with an exemplary embodiment, there is yet further provided a system, comprising a models database to receive one of the second model and the third model from the GPU and configured to use a neural network training method to set the rank by training a first portion of the dataset, assess the accuracy of the second model based on a second untrained portion of the dataset and to store the second model in the models database based on the assessment.

In accordance with an exemplary aspect, there is yet further provided a computer controlled system for predicting a mental state of a user comprising a processor that is configured to: provide a first model for prediction of a mental state of the user based on non-physiological data gathered from a first group of users; provide a second model for prediction a mental state of a user based on physiological data gathered from a second group of users; receive data of a tested user; associate at least one model of said models to the tested user based on a highest rank of user mental state predictability of the associated model compared to a rank of user mental state predictability of other models of the at least one model; predict the mental state of the user using the associated model; and dynamically modify the associated model in case that the rank of user mental state predictability of the modified model is higher than that of a previously associated model.

BRIEF DESCRIPTION OF THE DRAWINGS

The accompanying drawings, which are incorporated into and form a part of this specification, illustrate one or more example aspects of the invention and, together with the detailed description, serve to explain their principles and implementations:

FIG. 1D illustrates non-limiting examples of stored data, in accordance with certain exemplary embodiments of the presently disclosed subject matter.

FIG. 2 illustrates a non-limiting generalized flow-chart example of the labelling module, in accordance with certain exemplary embodiments of the presently disclosed subject matter.

DETAILED DESCRIPTION

Figure 1A:
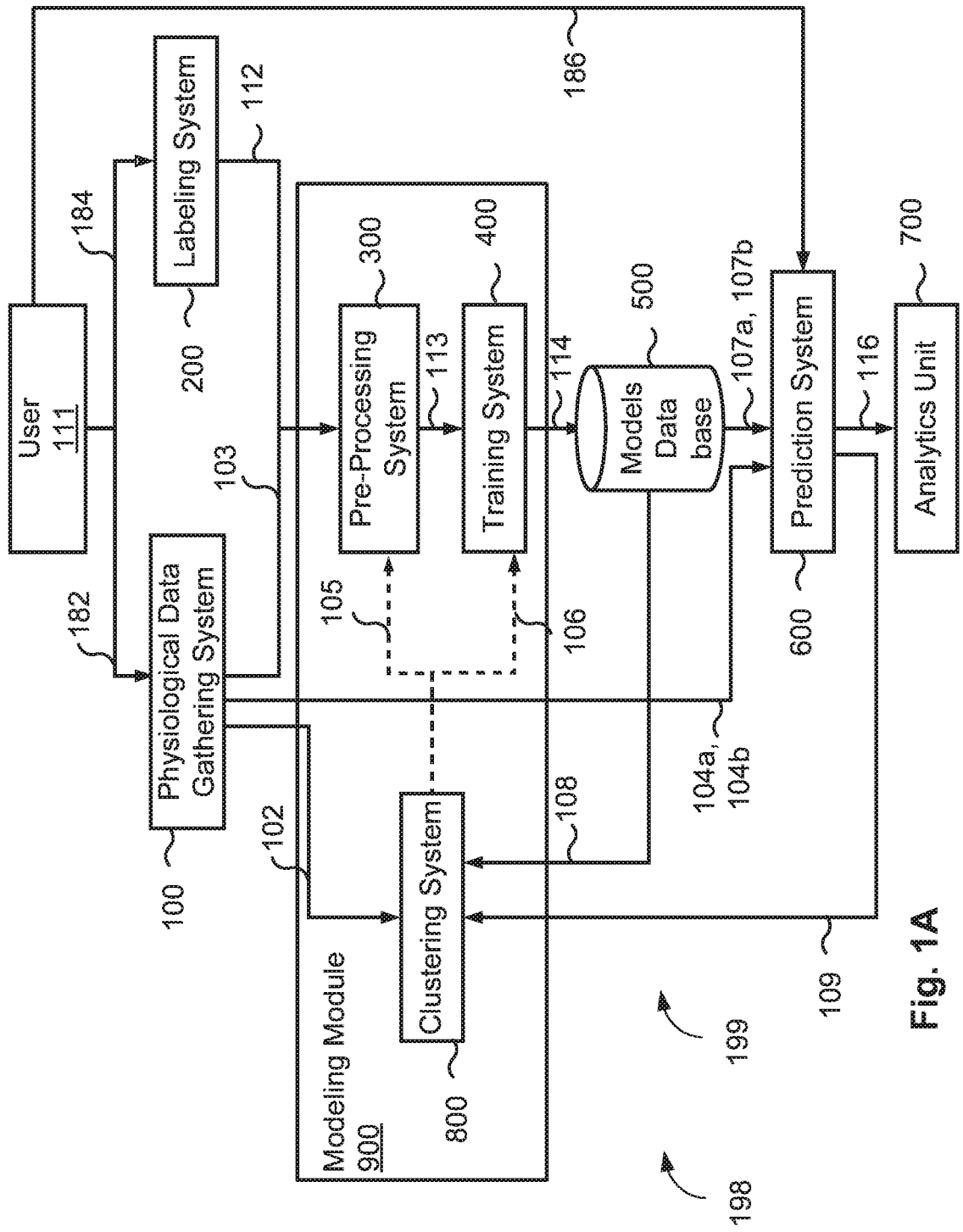
FIG. 1A illustrates a generalized example architecture and flow-chart diagram of the method and system of modelling human emotional states and/or mental states, in accordance with certain exemplary embodiments of the presently disclosed subject matter.

In the following detailed description, numerous specific details are set forth in order to provide a thorough understanding of the invention. However, it will be understood by those skilled in the art that the presently disclosed subject matter may be practiced without these specific details. In other instances, well-known methods, procedures, components and circuits have not been described in detail so as not to obscure the presently disclosed subject matter.

Unless specifically stated otherwise, as apparent from the following discussions, it is appreciated that throughout the specification discussions utilizing terms such as "processing", "computing", "representing", "comparing", "generating", "assessing", "matching", "updating" or the like, refer to the action(s) and/or process(es) of a computer that manipulate and/or transform data into other data, said data represented as physical, such as electronic, quantities and/or said data representing the physical objects.

Discussions herein utilizing terms such as, for example, "providing", "receiving", "modelling", "associating", "modifying", "determining", "generating", "predicting", or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information storage medium that may store instructions to perform operations and/or processes.

Moreover, the terms "plurality" and "a plurality", as used herein, include, for example, "multiple" or "two or more". For example, "a plurality of items" includes two or more items.

References to "one embodiment", "an embodiment", "demonstrative embodiment", "various embodiments", "exemplary embodiments", etc., indicate that the embodiment(s) so described may include a particular feature, structure, or characteristic, but not every embodiment necessarily includes the particular feature, structure, or characteristic. Further, repeated use of the phrase "in one embodiment" does not necessarily refer to the same embodiment, although it may.

As used herein, unless otherwise specified, the use of the ordinal adjectives "first", "second", "third" etc., to describe a common object, merely indicate that different instances of like objects are being referred to and are not intended to imply that the objects so described must be in a given sequence, either temporally, spatially, in ranking, or in any other manner.

The term "computer" and/or "computing system" as used herein, includes, for example, any kind of hardware-based electronic device with data processing capabilities, including, by way of non-limiting example, a personal computer, a server, a computing system, a communication device, a processor or processing unit (e.g. digital signal processor (DSP), a microcontroller, a microprocessor, a field programmable gate array (FPGA), an application specific integrated circuit (ASIC), etc.), and any other electronic computing device, including, by way of non-limiting example, the processing circuitry therein, including, by way of non-limiting example, various hardware processing circuitries disclosed in the present application, such as for example 122, 303 and others.

The term "mental state" and/or "emotional state" as used herein, includes, for example, any kind of psychological condition and/or reaction, either mental and/or physiological, of the human body suitable to the presently disclosed subject matter.

The term "stress" as used herein, includes, for example, any kind of human emotional and/or mental and/or physiological response to different events and/or challenges and/or environments suitable to the presently disclosed subject matter.

The terms "non-transitory memory" and "non-transitory storage medium" as used herein, include, for example, any volatile or non-volatile computer memory suitable to the presently disclosed subject matter.

It is to be understood that the term "signal" as used herein, may exclude, for example, transitory propagating signals, but may include, for example, any other signal suitable to some demonstrative embodiments.

The term "data aggregation" as used herein, includes, for example, a process in which information is gathered and expressed in a summary form such as data structures.

The term "database (DB)" as used herein, includes, for example, an organized collection of data stored, for example, at a memory of a DB server, which may be a dedicated computer to hold the DB and to run a dedicated software, for example, to collect, store and manage the data of the DB. For example, the DB may store one or more data structures, which include a collection of schemas, tables, queries, reports, views, and other elements.

The term "module" as used herein, includes, for example, any hardware component, a software and/or any combination of software and hardware, which may be embedded on a computing system, such as, for example, a processor.

In some demonstrative embodiments, databases may include, for example, a cloud DB, DB server, an in-memory DB, an active DB, distributed DB, an embedded DB, an End-user DB, SQL DB or the like.

One of the aspects of a system, according to certain embodiments of the presently disclosed subject matter, of modelling an emotional state and/or a mental state of the user, is to provide an ongoing monitoring of a user, e.g. a human, his/her emotional state and/or mental state, in a digitally quantitative way. One non-limiting example benefit from creating such a system, in some examples, is to enable the users to monitor their emotional state and/or mental state(s) over time in a reliable and consistent way, thus enabling a better understanding of the connection between the user's physiological and mental states.

Providing such a system can, in some examples, enable credible monitoring of emotional and/or mental states, such as, for example, stress and/or anxiety and/or depression and/or other states. In some cases this can enable a wide range of solutions to engage, for example, with stress problems, identify them, and potentially affect them positively.

An example computer-controlled system, that in some cases is configured for modelling at least one of a mental state of a user and an emotional state of a user, is disclosed herein. The example system includes a processing circuitry, which can be configured to provide one or more model(s) for prediction of a mental state and/or emotional state of the user. These models include one or more first models based on non-physiological data gathered from a first group of users, and/or on one or more second models based on physiological data gathered from a second group of users, and/or on a third model based on physiological data gathered from this user solely. These models may be referred to as a set of models. The processing circuitry of the system also receives data of a tested user. The processing circuitry of the system in some examples can then associate at least one model of the set of models to the tested user, based at least on a highest rank of user state predictability of the associated model compared to a rank of user state predictability of other models of the set of models. The rank of user state predictability is in some examples indicative of the mental and/or emotional state of the tested user. The association of a model to the tested user can in some examples be based at least partly on association model(s).

In some examples the processing circuitry is further configured to dynamically modify the association of the user to a prediction model, in an automated fashion, in response to determining that a rank of user state predictability of another prediction model is higher than a rank of user state predictability of a previously associated prediction model. This determination is in some models based at least partly on monitoring of physiological data of the tested user. The other model is set to constitute the associated prediction model.

In some examples the processing circuitry is further configured to generate an individual model. The processing circuitry may also associate the individual model to the tested user, based at least on a highest rank of user state predictability of the individual model compared to a rank of user state predictability of the previously associated prediction model. In some cases, this can be based at least on the rank of user state predictability of the models of the set of models not meeting a threshold. In some examples, if the user state predictability rank of a model previously associated with a user is below a threshold of 65%, and if the individual model has a rank above this threshold, the user is associated with the individual model in place of being associated with the previously associated model.

In some examples the processing circuitry is further configured to predict the mental and/or emotional state of the tested user using the associated model.

The presently disclosed subject matter also discloses example methods of training and generating association model and prediction models, and of re-training them. Details are disclosed further herein.

FIG. 1A below provides an overview of an example system for modelling a human emotional state and/or mental state, along with flows between components. FIGS. 1B to 7 provide details of the components of FIG. 1A, including flows between components. After these figures, an example scenario based on registering a new user and collecting data for the user, is described, while making use of the components disclosed with reference to FIGS. 1A to 7. Example flowcharts are presented in FIGS. 8A to 9.

Turning first to FIG. 1A, it illustrates a generalized example architecture and flow-chart diagram of the method and system of modelling a human emotional state and/or mental state, in accordance with certain embodiments of the presently disclosed subject matter. It is noted that the data flow 199 depicts an example architecture of functionalities and systems, and flow of information between them. In some examples, all elements of FIG. 1A, with the exception of the user, may be referred to as the system 198 of modelling a human emotional state and/or mental state.

In some demonstrative embodiments, the inputs to the system come from a user 111 that provides the system with two major inputs: physiological information (referred to herein also as "data") 182 and emotional and/or mental state time markers (referred to herein also as "labels") 184. These two inputs are processed by the physiological data gathering module 100 (also referred to herein as physiological data gathering system) and by the labelling module 200 (also referred to herein as labelling system), correspondingly. More details of some examples of the functions of systems 100 and 300 are disclosed further herein with reference to FIGS. 1C and 2. It is also noted that in some examples, the user 111 also provides metadata input 186 to prediction system 600. In some examples the inputs 182 and 184 are processed in order to be used, in parallel, for the following functionalities.

In some demonstrative embodiments, the system of modelling a human emotional state and/or mental state may include a modeling module 900. Modeling module 900 may include a preprocessing module 300, a training module 400 and a clustering module 800.

In some demonstrative embodiments, modeling module 900 can be configured to generate at least one of a first model based on non-physiological data gathered from a first group of users, a second model based on the one or more labels and the physiological data gathered from a second group of users, and a third model including an individual model configured to predict a mental and/or emotional state of an individual user. Moreover, each one of the first model, the second model and the third model is associated with a rank of a user state predictability configured to facilitate prediction of the mental state of the tested user as described below, for example. User state predictability herein refers in some examples to predictability of the mental and/or emotional state of the user. It is also noted that for brevity of exposition, in the presently disclosed subject matter the term "mental state" is sometimes used as a term to refer to both mental state and/or emotional state. In some demonstrative embodiments, the rank of user mental state predictability may be determined according to physiological data of the tested user which are gathered over the time frame.

For example, for a model of the first, second and third models, the modelling module 900 can be configured to predict the mental state of the tested user based on at least a portion of said gathered data, and compare said predicted mental state with a corresponding mental state, as indicated by a label of said labels, and determine said rank associated with the model according to one or more performance metrics of said comparison.

For example, it is also possible that labels will be provided using other methods, for example a priori knowledge from a controlled environment, such as an experiment, for example.

In some demonstrative embodiments, modelling module 900 may be configured to associate the tested user to the model of the first, second and third models having the highest rank of the user mental state predictability.

For example, the first model and the second model may be arranged in one or more clusters, a cluster of the one or more clusters comprising at least two users having at least one of common physiological data and common non-physiological data (whether fully common, or in some cases partly common, e.g. they have at least one characteristic in common).

The first functionality of a system performing flow 199 may include creating and/or training and/or optimizing models. For example, the data and labels serve the next stage, e.g. the Pre-processing system 300, as raw data input 103, 112 for the generation of datasets. A dataset is a basic element which may be required to train a model (combined with a preconfigured worker). More information regarding datasets creation and workers configuration will be described below with reference to FIGS. 3A and 4. The Pre-processing system 300 is configured to make calculations in order to normalize and/or manipulate and/or process the data and/or labels, so that they can be used as a dataset by the training module.

As mentioned above, the Pre-processing module 300 is configured to generate datasets. The generation of datasets is orchestrated by the clustering module 800, which guides 105 the Pre-processing module 300, for example indicating which user's data and labels module 300 may use in order to generate a dataset. For example, module 300 may be instructed to generate a dataset which consists of data and labels, for example, from only a cluster of users who are 35 years old or younger. Further information regarding the orchestration functionality will be provided below. Many kinds of datasets may be created based on different kinds of clusters, for example, non-physiological (metadata) clusters, physiological clusters, and/or any other clusters. Training of the association models, including in some cases based on non-physiological clusters, may make use of physiological data of the users, in the cluster dataset, referred to herein also as second physiological data. More details of some examples of the functions of system 300 are disclosed further herein with reference to FIGS. 3A and 3B.

The kind of cluster will determine what kind of model will be trained later in the process. The clustering module 800 is configured to generate multiple clusters and for each cluster it orchestrates a creation of a corresponding dataset. Thus, the dataset, as explained above, determines which kind of model will be produced and therefore it dictates the module's 400 capability to produce many kinds of models.

Having multiple kinds of models enables highly accurate prediction of emotional and/or mental states, for example, stress, anxiety, depression, etc., as the system is constantly evaluating which model has the best performance for each individual user (which model has the optimal rank in general and/or for each user individually), e.g. as described below.

Once a dataset is ready, it is sent 113 to the training module 400 to serve as one input for a training process. The dataset input may be accompanied by a preconfigured worker (which may be produced independently in the training module 400, for example), in some embodiments, based on preconfigured tasks. In other embodiments the dataset input may be produced based on tasks sent 106 from the clustering module 800. Both are used by, for example, one or more graphic processing unit (GPU) servers that run, for example, a neural network training method, in order to train one or more models and to evaluate each model's rank accordingly. Rank may be used to determine which model has the optimal prediction performance for each user of the system individually. Ranking for each user has a benefit, for example, in terms of customizing which model will be associated for each user (one model may perform better on user A than it will perform on user B, etc.), thus, enabling a more personalized prediction and accuracy. In some examples, this greater accuracy may have certain advantages, for example facilitating prevention of accidents, illnesses and improving general wellbeing.

For example, based on neural network techniques, one or more models are trained. The training function may utilize a certain percentage of a dataset (usually 70%-80% of the dataset), and make an assessment of its prediction performance based on the other unused percentage of the dataset (usually 20%-30% of the dataset). This unused percentage of the dataset may be referred to in some examples as an untrained portion of the physiological data. The assessment serves as a basis for making a decision whether the new trained model is contributing to improvement of accuracy or not, and therefore whether or not it will be sent 114 to the models database 500. In addition, the assessment serves as a basis for giving each trained model a rank (which may involve also time performance, memory utilization, etc.). The ranking method that the system provides will be further described below in accordance with certain embodiments of the presently disclosed subject matter. Additional details of exemplary functions of system 400 are disclosed further herein with reference to FIG. 4.

The models database 500 and particularly the prediction model flow and/or progressive accuracy improvement may be elements of the one or more embodiments, e.g. as described below with reference to FIGS. 5A and 5B.

The second functionality of a system performing flow 199 can include monitoring and/or predicting emotional and/or mental state of a human, e.g. as described below.

The physiological data (without labels) may be sent 104A, 104B to the prediction module 600, where it can used by a monitoring unit as an input, for a prediction model to monitor and/or predict the user's emotional and/or mental state.

This part of the system provides output that may be of value to the user: it is a prediction of the emotional and/or mental state of the user. This module may provide, for example, a prediction of the user's mental state based on the physiological data of the user, without using input labels. The results of the prediction can be sent 116 to an analytics unit 700 for generating aggregated business insights, e.g. as described below.

From the users' point of view, physiological data is provided, for example, by using a sensing unit, and certain feedback inputs, e.g. labels, and thus obtain an ongoing and accurate monitoring and/or prediction of their emotional and/or mental state, for example, their stress condition.

The third functionality of a system performing flow 199 can include clustering users by their similarities, e.g. as described below, for example with reference to FIG. 7.

The physiological data, for example, without labels, may be sent 102 to the clustering module 800 where it can be used in order to create groups, e.g. clusters, of users based on similarities in their physiological patterns, e.g. as described below, for example with reference to FIG. 7.

As mentioned above, the first functionality output may be used to train different kind of models. The models (e.g. all models) are stored in the models database 500. This database stores multiple models of different kinds, e.g. as described below with reference to FIG. 5.

The system may include a first kind of models which are trained based on a dataset from specific groups (e.g., clusters) of users that were clustered in the clustering module 800 based on their non-physiological data/profile (for example: gender, age, nationality, etc.). This is a basic kind of model and its advantage is that once a user is registered to the system (and, for example, has provided some personal details), the system can associate the user with a model instantly and/or almost instantly. The first kind of models may be referred to herein as metadata models, subject to the presently disclosed matter. In some examples, the creation of such a metadata model involves sending 109 of metadata of a newly registered user from Prediction System 600 to Clustering System 800, for example as disclosed with reference to FIG. 7.

The system can include a second kind of models that are trained based on a dataset from specific groups (e.g., clusters) of users that were clustered based on similarities in their physiological data. This is a more advanced kind of model and its advantage is that once a user has already used the system and provided physiological information (for example, during a day or week of monitoring), it can be associated with a model which may fit better to the user's physiological patterns. In some examples, this enables the system to provide better predictability (prediction performance). The second kind of models may be referred to herein as physiological models, subject to the presently disclosed matter.

Moreover, the system can include a third kind of models which are trained based on a dataset from one individual's physiological data and labels (e.g., dataset). This is an advanced kind of model. One advantage is that once a user has used the system for a certain period and has provided a substantial amount of personal feedback, e.g. labels, the user can be associated with an individual model. This is a customized and adaptive model, which fits for a specific user and therefore may provide a personalized and/or higher predictability (e.g., prediction performance). The third kind of models may be referred to herein as individual models, subject to the presently disclosed matter.

In some exemplary embodiments, other models may also be trained. One non-limiting example is a model that was trained based on a dataset of all users' data and labels that exist in the system ("global model"). The advantage of such a global model is that it may provide prediction for users that did not register to the system, and/or for a user who registered to the system, but did not provide metadata and/or physiological information. More on the models stored in the models database is disclosed, for example, with reference to FIG. 5.

Training of the first, second, third and/or any other kind of models may be performed every certain time frame, for example once a day. For each given training, a model may be evaluated, ranked and compared with the current rank of each individual's currently associated model. In case that the newly trained and/or optimized model has a higher rank, for example, better predictability performance, for a particular user, than the model which is currently associated with that user, the system will associate the higher ranked model to each user individually. More on training of models is disclosed, for example, with reference to FIG. 4.

In some exemplary embodiments, the system for digitizing human emotions and/or mental state may train multiple kinds of models over time (and many types of models within each kind of models). One purpose of the multiple models is to enable dynamic association of different models to different users which results in a progressive accuracy improvement over time for each user individually as described below, for example.

The prediction module 600 is constantly and dynamically evaluating the associated prediction model per each user. In particular, it is constantly checking for promoting the user to a more accurate model from the models database. For example, it may check if a certain user can be promoted from a metadata model (which has for example a rank of x) to a physiological model (which has for example a rank of 2x). The term "more accurate kind of model" should be construed to include, for example, a model which received a higher rank and therefore is expected perform better for each user individually in terms of predictability. The rank-based model promotion process will be described in detail below.

Once a better prediction model (a prediction model which has a higher rank) was found for a user in the models database 500, the prediction module associates it to the particular user, thus enabling a constant improvement and/or personalization of the prediction function and its performance. The model provides a better and more accurate prediction output for each user individually, as the more times the user uses the model, the more data is gathered, and more accurate and personalized models can be trained for the user. More details of some examples of the functions of system 600 are disclosed further herein with reference to FIG. 6.

Compared to current existing solutions, the proposed system offers in some examples a major paradigm shift, in that it enables an association of a model (from a pool of models stored in models database, for example) to each user individually ("user-oriented system"), and is not focused on improving the model(s)' performance so that the performance will match as many users as possible ("model-oriented system"). In some examples, this complies with real-life, where there may be a large variance and diversity between individuals' physiological reactions to emotional and/or mental states, therefore challenging the "model-oriented" existing solutions' performance and capabilities. Current solutions tend to focus only and/or mainly on perfecting one kind of model (for example: a Global model as described above). By contrast, in some examples this system has a different heuristic that is more robust: to train as many kinds of models and types of models as possible, rank them, and then associate each user with the most fitting model, based on ranking and performance. In some examples, the presently disclosed system and method provide a technical solution that automatically, in a dynamic fashion, changes the association of a user to a model, for example by determining a rank of the model, and comparing this rank to the rank of a model currently associated with the user, and associating the user with the model of the higher rank. In some examples, this technical solution can facilitate the association of the user to a more optimal model for him/her. This in turn can in some examples enable better prediction of their emotional/mental state at a point in time, based on physiological data at that point in time.

In some examples, the presently disclosed subject matter can provide at least certain example advantages, compared to at least some other techniques. Receiving an accurate output of an emotional/mental state, which is based on physiological measurements, in some cases based on physiological data of one individual, in some examples of the presently disclosed subject matter, can enable earlier detection of problematic events and patterns, since the method is sensitive to changes, in various physiological parameters, on a personal level. In some examples, this is significant for providing comparatively early detection. By comparison, for example, in some cases of camera-based emotional sensing, by the time there is a facial expression, detection of the problematic emotional state may be too late. In addition, some mental states might be on a level of which the users are unaware, or where the user does not necessarily know that he or she is going through a certain emotional/mental experience. In at least this sense, physiological-based measurement and analysis can provide an earlier, as well as a more accurate, solution.

Also, in a prediction of an emotional/mental state based on physiological data, in some cases based on physiological data of one individual, the analysis in some examples is agnostic to cultural and geographic differences. This in some cases is advantageous, enabling deploying this technology to the mass market, at a global level, and in countries with different cultural/ethnic mixes and regional variations within the country. In such markets, each user can be different from the other, and yet accurate performance of prediction is to be provided for all users.

In some demonstrative embodiments, clustering system 800 of the system of modelling a human emotional state and/or mental state may include at least two features as described as follows.

The first feature or functionality may be orchestrating dataset creation for training of the prediction model(s), and the second feature may be orchestrating dataset creation for training of association model(s). Prediction model(s) may be used for predicting the user's emotional and/or mental state. Association model(s) may be used to associate a user with a cluster, and therefore to associate the user with the highest performing prediction model of the associated cluster.

For example, as described above, the system may include creation of different clusters of users based on different criteria, e.g. non-physiological (metadata), physiological, individual, and the like, which is used to orchestrate the Pre-processing module 300 concerning which datasets it should generate for training. When orchestrating the training of prediction models, and the creation of datasets for such training, the clustering system 800 may use as an input one or more association models received 108 from models database 500.

In some examples, the clustering module 800 has a second feature or functionality, of orchestrating the generation of a dataset(s) and orchestrating a corresponding task for training association model(s). According to an exemplary aspect, the association models can be used for two or more purposes: (a) associating individuals to different kinds of clusters (the clusters are used to orchestrate generation of datasets, for example, in the preprocessing module) and (b) for associating existing prediction models of modelling human emotional state and/or mental state to new and existing users of the system.

It is noted that the above described system is not bounded by the structure and/or architecture as described with reference to FIG. 1A.

Figure 1B:
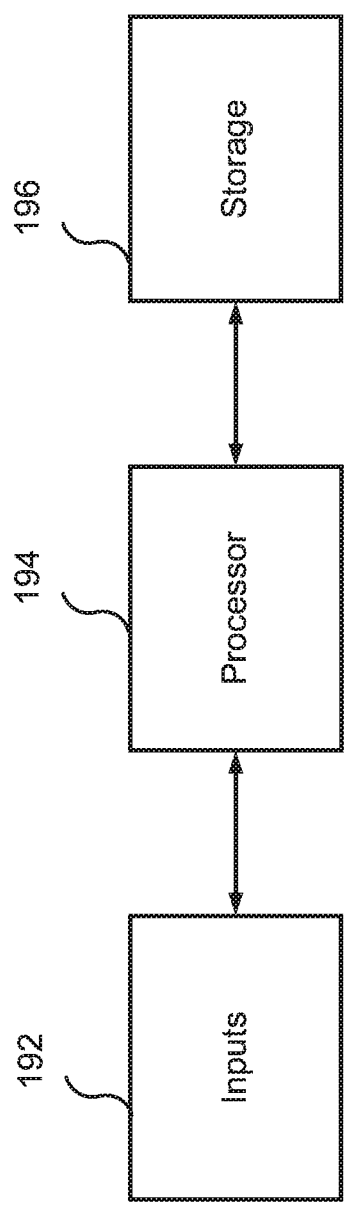
FIG. 1B illustrates a block diagram of a method and system of modelling human emotional states and/or mental states, in accordance with certain exemplary embodiments of the presently disclosed subject matter.

Turning to FIG. 1B, it illustrates a block diagram of a method and system of modelling human emotional states and/or mental states, in accordance with certain embodiments of the presently disclosed subject matter.

In some demonstrative embodiments, the block diagram includes an input block 192 to receive non-physiological and physiological data from the tested user, a processor 194 to generate a plurality of models as described above with FIG. 1A, and a storage 196 to store the models as described below.

Figure 1C:
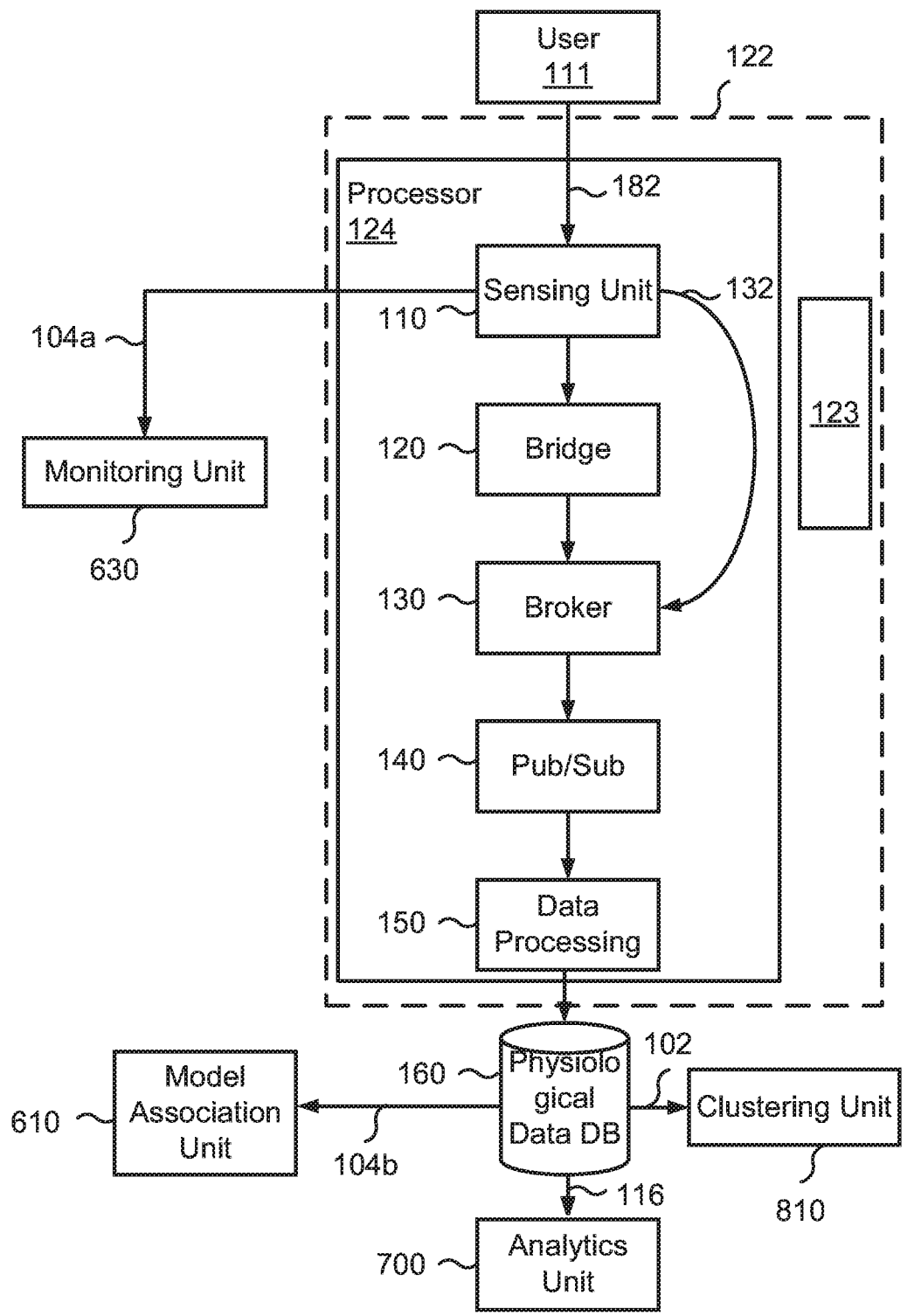
FIG. 1C illustrates a non-limiting generalized flow-chart example of the physiological data gathering module in accordance with certain exemplary embodiments of the presently disclosed subject matter.

Turning to FIG. 1C, it illustrates a non-limiting generalized flow-chart example of the physiological data gathering module, in accordance with certain embodiments of the presently disclosed subject matter.

In some exemplary embodiments, the method may measure different physiological parameters of an individual, also referred to herein as "data". Non-limiting examples of these parameters may be body temperature, heart rate, electrical skin resistance and/or other physiological parameter/s, and/or electrical signals (such as photons, voltage, etc.). Parameters are subject to change. The data may be collected from the user 111 directly through sensors, and/or may be calculated by using raw data and/or signals collected from the sensors, and/or by any other collection method.

In some examples, the collection of the parameters is performed using a sensing unit 110, which transmits the above collected parameters by radio frequency (RF) (such as WiFi, Bluetooth and/or any other wired/wireless transmission method, for example) to a bridge 120. The bridge 120 is a computing device (such as router and/or gateway and/or computer and/or other device, for example), which transmits incoming data from the sensing unit 110 to a broker component 130 (for example, in a cloud environment) using, for example, TCP protocols (such as HTTP and/or MQTT and/or any other protocol). It is also possible that the sensing unit 110 may transmit the data directly 132 to the broker 130 without going through the bridge 130, using, for example, TCP protocols (such as HTTP and/or MQTT and/or any other protocol). In addition, the sensing unit can transmit 104A the data directly and/or indirectly to a monitoring unit 630 of the prediction module 600 and serves as an input for the prediction module 600, e.g. as described below with reference to FIG. 6.

The broker 130 is responsible for decoding the data from the sensing unit's 110 communication protocol and for encoding to a different communication protocol which is commonly used in the cloud (not shown). It is possible, that the communication protocol will stay the same and not go through any decoding/encoding process.

After performing this calculation, the broker 130 sends the data to publish/subscribe (Pub/Sub) module 140, which may in some examples be software. The Pub/Sub 140 throttles and/or controls the data ingestion rate to data processing unit 150, in order to balance the servers' 150 load. From there, the data is sent to a data processing unit 150, a cluster of servers, for basic data manipulation (for example: change data schemes, remove invalid messages, etc.) and/or for ordering. After performing the processing, the data is sent to the physiological data database (DB) 160.

The physiological data database can also send 104B data to the model association unit 610 of prediction system 600, send data 102 to clustering unit 810 of clustering system 800, and send data 116 to the analytics unit 700, e.g. as described below.

In some exemplary embodiments, the analytics unit 700 may compute business intelligence metrics (BI) for the users of the system, for example, executive managers of an organization and/or supervisors and the like. Business intelligence can be used, for example, by enterprises to support a wide range of business decisions—ranging from operational to strategic. Basic operating decisions include work methodologies and adapting operational protocols. Strategic business decisions involve priorities, setting goals and directions at the broadest level according to the provided business intelligence.

The physiological data gathering system 100 may in some examples be a computer configured to execute the algorithms described herein. In particular, it may comprise, for example, processing circuitry 122 and physiological data database 160. In some examples, the processing circuitry 122 comprises processor 124 and a memory 123. In the example of the figure, the units 110, 120, 130, 140, 150 all run on processor 124. In other examples, some or all of the units may be separate hardware units, cloud-based components etc.

Turning to FIG. 1D, it illustrates non-limiting examples of stored data, in accordance with certain embodiments of the presently disclosed subject matter. The figure shows sample fields and sample values. Examples of data that are stored in this DB may be found in components 160a "physiological data" (containing, for example, device id, user id, organization id, physiological data sample array and more or other metadata) and 160b (physiological data sample information).

In some examples, user ID can be a number or string associated with the particular user/individual, and organization ID can be an ID corresponding to e.g. the user's employer/company. The "sample" field can be an array of physiological data sample in data structure 160b. In one example, the physiological data record 160a includes data for 1 second, and includes a field "sample". In the example, this field is an array or batch of multiple "sample" records 160b. For example, samples may be recorded ten times per second, and thus the sample array in each record 160a contains ten sample records 160b.

Sample data 160b can include, in some non-limiting examples SPO2, heart rate (HR), blood velocity (BVP), heart rate variability (HRV), skin temperature or other temperatures, blood flows 1-4, accelerometer measurements in three coordinates e.g. x, y, z (acc1, acc2, acc3), blood perfusion and pulse-related parameters, among other parameters. In some examples the parameter "motion value" can be calculated from the accelerometer measurements. The numbers in FIG. 1D are merely for illustration purposes.

The above system is not bounded by the structure and/or architecture as described with reference to FIGS. 1B, 1C and 1D.

Turning to FIG. 2, it illustrates a non-limiting generalized flow-chart example of the labelling module 200, in accordance with certain embodiments of the presently disclosed subject matter.

Labelling module or system 200 can in some examples be a computer. It can comprise, for example, a processing circuitry 212 and labels data database 220. The processing circuitry 212 may in some examples comprise a processor 214 and a memory 216. The processor 214 may comprise labelling unit 210. In some examples, unit 210 is a software module or component.

In some demonstrative embodiments, labelling module or system 200 generates labels which are markers in time (time markers) that indicate a certain mental and/or emotional state at time marks, e.g. points of time, in a certain time frame. A mental state may be, for example, stress, relaxation and/or and other mental and/or emotional state. For example (220a), a label sample record in the labels database 220 will contain user id, start and end timestamps, value of the mental state (e.g. stress, depression, relaxation, etc.) and potentially more information, as may be required. The numbers in 220a are merely for illustration purposes. In some examples, the labels are indicative of the mental and/or emotional state of the user. In some examples, the labels correspond to at least a portion of the physiological data of the user.

In some examples, the labels are generated in labelling unit 210, based on at least two methods: (1) a priori knowledge (2) feedback received from a user.

In some examples, the first labelling method 205 is based on gathering the physiological data during sessions with a known a priori emotional and/or mental state of a user, e.g. an individual. For example, the mental and/or emotional state may be induced based on common academic and clinical methods, if desired. In one non-limiting example, the user is instructed to read a sequence of written passages, where each is known with a probability to elicit a specific emotional state (e.g. mild sadness, profound sadness, happiness, stress and the like) In another non-limiting example, the user is instructed to perform a sequence of tasks, where each is known, with a probability, to elicit a specific emotional or mental state (stress, frustration, satisfaction, confidence and the like). During the sessions, time markers are saved to the cloud, or to other storage, which state the exact a priori mental and/or emotional state of the user, e.g. individual, for a specific time frame.

The second method 203 of labelling is based on feedback 184 received from a user. In some examples, the system sends a notification informing the tested user (e.g., participant) of his/her current emotional state. Sometimes, the system will send the notification because it predicts that the emotional state has changed, and sometimes it will send it randomly. For example, sending it randomly may be used to check the user's feedback credibility. The user enters his feedback. The module saves the feedback time along with the feedback itself in the labels database. The feedback time may be associated with a window of time that is subject to change, but is subject to the idea that from a set time, data is labelled at X number of minutes before and Y number of minutes post the time.

Later on in the process, the labels stored in database 220 can enable the training of a model(s), e.g. as described below.

The above module is not bounded by the structure and/or architecture as described with reference to FIG. 2.

Figure 3A:
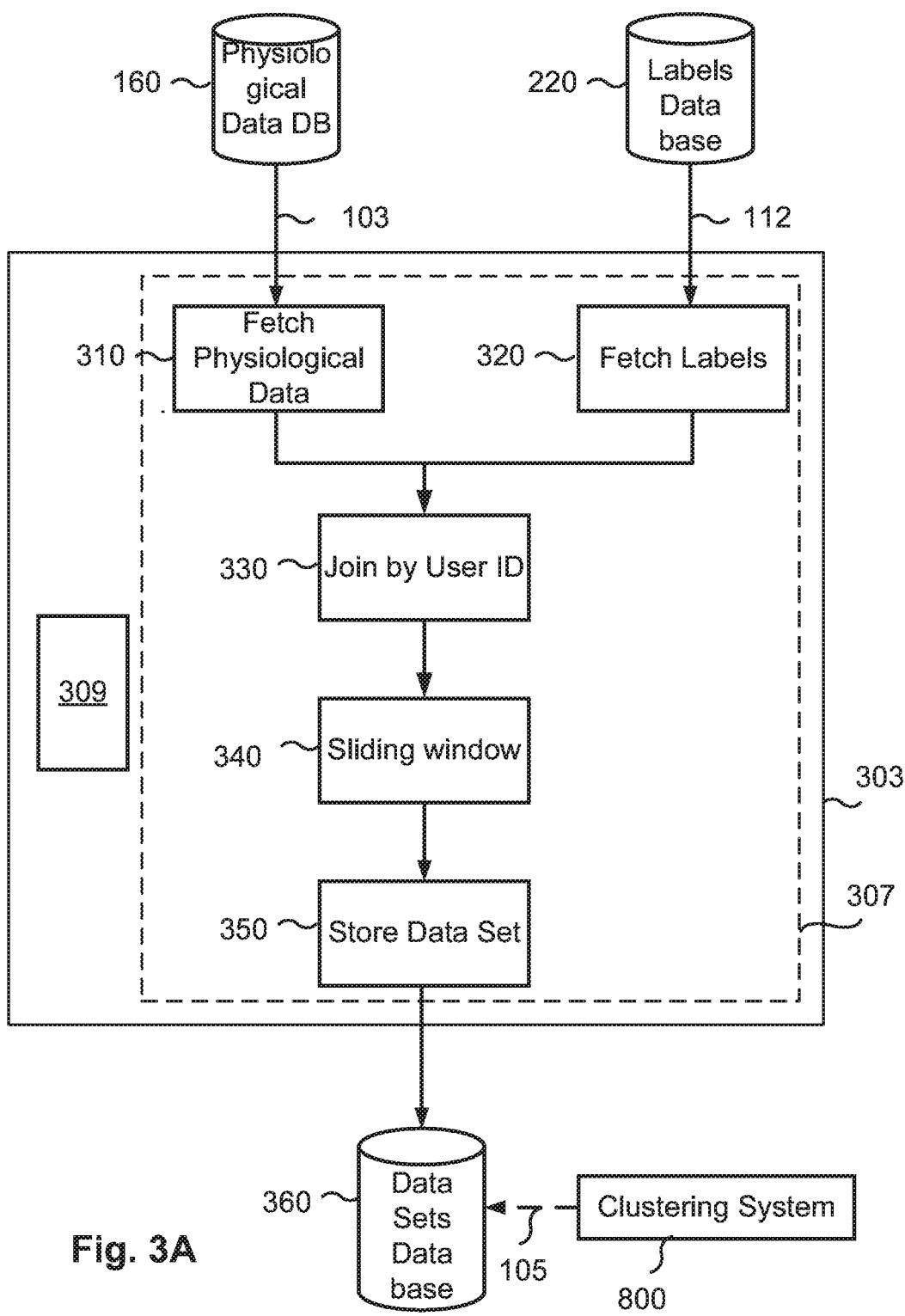
FIG. 3A illustrates a non-limiting generalized flow-chart example of a Pre-processing module, in accordance with certain exemplary embodiments of the presently disclosed subject matter.

Turning to FIG. 3A, it illustrates a non-limiting generalized flow-chart example of the Pre-processing module 300, in accordance with certain embodiments of the presently disclosed subject matter. Pre-processing module or system 300 may in some examples be a computer. It can comprise, for example, a processing circuitry 303. The processing circuitry 303 may in some examples comprise a processor 307 and a memory 309. Module 300 may also comprise the data sets database 360. FIG. 3A shows, within processor 307, a flow chart of steps 310, 320, 330, 340 and 350, that can in some examples be performed by processor 307 of module 300.

In some examples, the outputs 103, 112 of Physiological Data Database 160 (of system 100) and Labels Database 220 (of system 200) serve as the input for Pre-processing module 300. The Pre-processing module 300 is configured to transform the physiological data from its original structure, to a structure which complies with the model and which can serve as a viable input for its training (also referred to herein as a dataset). In order to perform this function, in some examples the following operations are carried out by the module, for example, at a frequency of once a day. The order of the operations are subject to change.

The module 300 fetches 103 the physiological data from the object storage in database 160, where each row contains the physiological data along with the user ID to which the data belongs, and in some examples other information such as timestamps (block 310). There are many rows, and each row may contain a single sample. For example, the data (as described for example in 160a and 160b) may be split into multiple files, where each file stores all the data that has been collected over the space of, for example, one hour. For the sake of clarity, the above process is a simplified non-binding example and therefore it may be performed in a different method and/or process.

In parallel, the module 300 fetches 112 the labels, from the database 220, where each row contains parameters such as the user ID, the start and end time of the label, and the label itself (for example: mental state A or mental state B) (block 320). There are many rows and each row consists of a single sample. For the sake of clarity, the above process is a simplified non-binding example and therefore it may be performed in a different method and/or process.

In some examples, from this point the module 300 performs actions referred to as Join by User ID (block 330), which uses the outputs of blocks 310 and 320, and combines and/or joins them according to the user's user ID. The output will include a table with, for example, three or more columns, e.g. User ID, Data, labels and other data.

After combining and/or joining the data, the module 300 performs an action known as the 'sliding time window technique'(block 340). In some examples, the sliding window 340 can be described by the following definition: "A time period that stretches back in time from the present. For instance, a sliding window of two minutes includes any event that have occurred in the past two minutes. As events fall out of the sliding time window (in this example because they occurred more than two minutes ago), they will no longer match against rules using this particular sliding window". Thus, in some non-limiting examples, a multiplicity of data items, each data item corresponding to two-minute windows, can be generated. For the sake of clarity, the above process is a simplified non-binding example, and therefore it may be performed in a different method and/or process.

In some examples after block 340, the module 300 stores file(s) for each user, e.g., to a database, which in some examples contains an array of windows in addition to their labels (block 350). A window contains an array of raw physiological data sorted by time. The files are stored in the datasets database 360.

This DB includes physiological datasets 361 and cluster datasets 362. Note that in some examples, physiological data 182 is recorded for a user, but no labels 184 for that data are captured. In such an example, physiological datasets 361 may contain only physiological data.

Figure 3B:
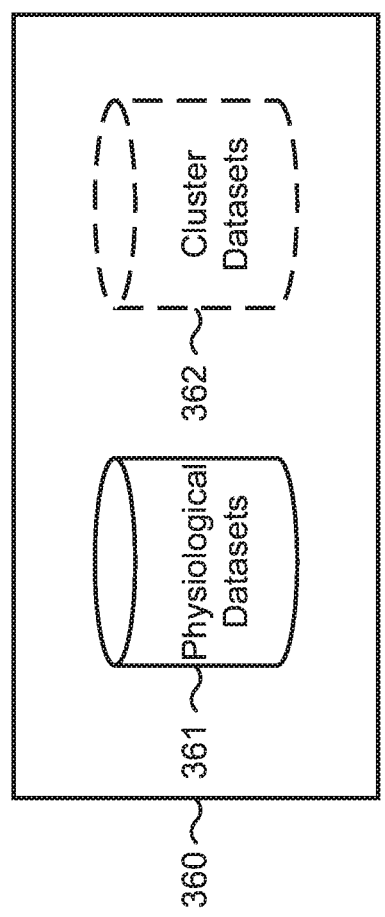
FIG. 3B illustrates a non-limiting generalized example schematic diagram of a data sets database, in accordance with certain exemplary embodiments of the presently disclosed subject matter.

Examples of datasets that are stored in this DB 360 can be found in components 361a and 361b in FIG. 3B.

The dataset generation process which may be performed, in the preprocessing module 300, as described in certain embodiments of the module, is in some examples orchestrated by the clustering module 800. Clustering module 800 may guide 105 the Pre-processing module 300 as to which user's data and labels it may use in order to generate a cluster dataset. For example, module 800 may instruct 105 data sets database 360 to generate a dataset which consists of data and labels, for example, from only a cluster of users who are 35 years old or younger. In other examples, system 800 instructs processor 307 of module 300 to generate this dataset while utilizing database 360. Further information regarding the orchestration functionality will be provided below, for example with reference to FIG. 7. Many kinds of datasets may be created based on different kinds of clusters, for example, non-physiological (metadata) clusters, physiological clusters, and/or any other clusters.

Turning to FIG. 3B, it illustrates a non-limiting generalized example schematic diagram of the data sets database, in accordance with certain embodiments of the presently disclosed subject matter.

The data sets database 360 can include physiological datasets 361 and cluster datasets 362. Cluster datasets 362 can be created per the guidance 105 of the clustering system 800. Examples of datasets that can be stored in this DB 361 can be found in components 361a and 361b. In some examples, the fields User ID and Organization ID are similar to those in FIG. 1D. In some examples, the "batches" field of 361a is an array of multiple individual batches 361b of physiological data—in some cases with labels. In some examples, the "label" field of 361b corresponds to the label field 112 received and processed by processor 307. In some examples, the "samples" field of 361b corresponds to the samples field of physiological data record 160a, containing an array of physiological data samples 160b. It is noted that datasets of DB 362 may in some examples have records similar in structure to 361a and 361b.

The above module is not bounded by the structure and/or architecture as described with reference to FIGS. 3A and 3B.

Figure 4:
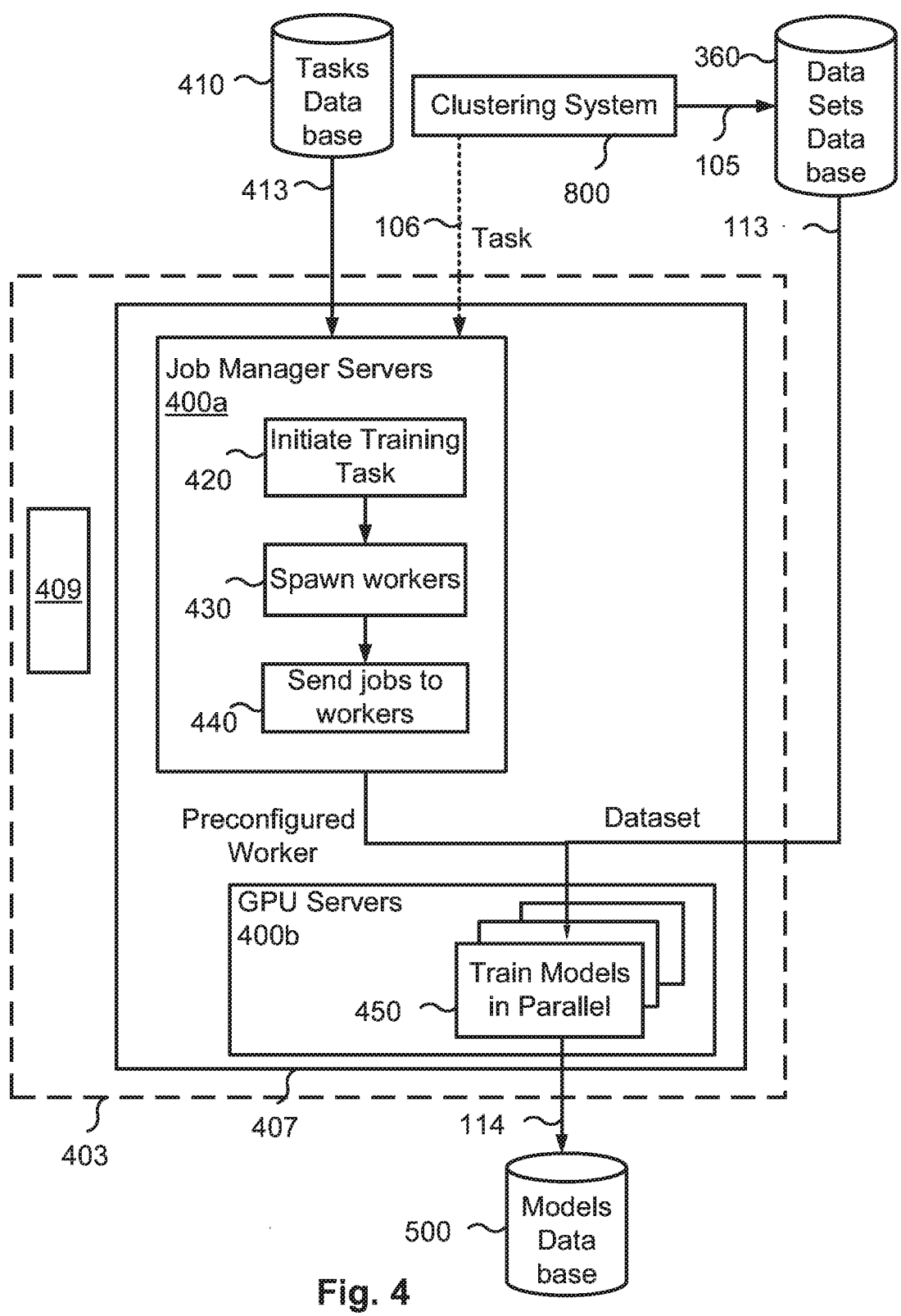
FIG. 4 illustrates a non-limiting generalized flow-chart example of a training module, in accordance with certain exemplary embodiments of the presently disclosed subject matter.

Turning to FIG. 4, it illustrates a non-limiting generalized flow-chart example of the training module 400, including a generalized neural network training environment, configured in accordance with certain embodiments of the presently disclosed subject matter. Training module or system 400 may in some examples include job manager servers 400a and graphic processing units (GPU) servers 400b. In some examples, system 400 may be a computer. The computer may, by way of non-limiting example, comprise a processing circuitry 403. The processing circuitry 403 may, in some examples, comprise a processor 407 and a memory 409. In the example of FIG. 4, the two servers 400a and 400b run on processor 407. In some other examples, each of the servers 400a and 400b may be a separate computer (or each may be a multiplicity of computers). Training system 400 may also comprise the tasks database 410. FIG. 4 shows, within manager servers 400a, a flow chart of steps 420, 430, and 440, that can in some examples be performed by servers 400a. FIG. 4 also shows, within GPU servers 400b, a flow chart, step 450, that can in some examples be performed by servers 400b.

The output 113 of datasets database 360 (of pre-processing system 300), and the output 413 of tasks database 410, may serve as the input for the training module 400. In some examples, generation of the models includes training the models according to a neural network method. In some examples, the training module 400 is designed to use the above components as inputs in order to train, for example, a neural network model. It is noted that in some examples, a model can only be trained using physiological datasets that are associated with labels as shown in 361 and 361b, for example.

For example, in order to train a neural network model, a preconfigured server (e.g. worker), may be produced. This production process may be done in the job manager servers 400a, which in some examples is a cluster of standard servers. In the example of the figure, one server is shown. In some examples, in the tasks database 410 each row or other record represents a task, e.g. a training session, including all the relevant parameters for executing this session. Examples of such parameters may include the number of layers of the neural network, window size, activation function for each neuron, number of neurons for each given layer and the like. The clustering system 800 may produce a relevant task 106, sent to server 400a of training module 400, and the task is stored e.g. in database 410. In another example, the task 106 is sent to and stored in database 410, and the task is then provided to job manager servers 400a. In still other examples, system 400 performs the task 106 without utilizing a database 410.

In some examples the training session will later run on block 450 performed by GPU servers 400b, as described below. For example, a task in database 410 may include an ID of a dataset in datasets database 360, a path to an output model in models DB 500, as well as jobs (micro-tasks) which indicate how to split the session to multiple servers (for performance optimization) etc.

In order to produce a preconfigured server (e.g., worker), first, a task is initiated by the job manager servers 400a, which pulls the task from the tasks database 410 and estimates required computing resources for executing the task (block 420). Next, the job manager servers 400a spawn servers (e.g., workers) (block 430). The workers serve to execute the training session in block 450. Then the jobs (micro-tasks which are included in a task) are assigned or sent to the servers (e.g., workers), that were spawned (block 440).

After completing the process at the job manager servers 400a, the preconfigured servers (e.g., workers) are sent to the GPU servers 400b, along with sending 113 one or more datasets from datasets database 360. In some examples, these are used for training a model in a training session (block 450). In block 450, models may be trained in parallel.

The process of the training sessions 450 may be to train, for example, neural network models (based on public knowledge, using known techniques). The output for this process is a trained model which is then stored 114 on the models database 500.

Before storing a trained model in the models database 500, block 450 in some examples conducts an assessment process of each model. In some examples, the assessment process serves two functionalities:

The first assessment functionality may be to assess whether the trained model has passed a predefined objective threshold (e.g., 95% accuracy rate, training time of less than 1 hour, etc.). Each model then receives an objective rank, which serves as a basis for evaluation whether or not this model is better than the existing model/s in the models database. In case that a model received a higher rank than an existing model(s) in the models database 500, it will be stored 114. In some examples, if the model does not receive a sufficiently high rank, it is not stored. This rank serves as a basis for making a decision whether or not the new trained model is contributing to predictability, and therefore whether or not it will be sent to the models database 500. In some examples, the new trained model is stored in 500 together with its rank.

For example, the training function may utilize a certain percentage of a dataset (in some examples 70%-80% of the dataset) and make an assessment of its prediction performance based on the other unused percentage (e.g., an untrained portion) of dataset (in some examples 20%-30% of the dataset). The prediction performance alongside other parameters, e.g. memory utilization, computing resources and/or other parameters, are used to determine an objective rank for each trained model. In other examples, models trained using machine learning methods undergo both validation and testing processes, for example using known techniques. In such a case, part of the untrained portion of the dataset can be used for the validation, and the remainder of the untrained portion can be used for the testing.

The second assessment functionality may be to assess relative ranks for the prediction model for each given user that is associated with the prediction model's cluster. The model's relative ranks may differ between different users of a given model's cluster. The relative ranks of the model serve as a basis for making a decision whether the new trained model is contributing to the predictability of each individual user's emotional and/or mental state or not. In case it is contributing to a predictability of a certain user, the newly trained model will be associated to this particular user to provide the user with higher prediction performance (to be explained further herein with reference to FIG. 6).

The ranking of models may be calculated, for example, according to the following methods: (1) a normalized (e.g., values from 0 to 1) combination of prediction performance metrics (e.g., accuracy, precision and recall). (2) a normalized combination of at least one computing performance metric (e.g., memory utilization, prediction time). (3) a normalized combination of at least one prediction performance metric and at least one computing performance metric. (4) a non-normalized combination of either at least one prediction performance metric and/or at least one computing performance metric. (5) another ranking method.

A first non-limiting example of determining rank of models, and comparing rank, is now presented. For example, physiological model P100 is trained using 70% of data set D100. Physiological model P200 is trained using 70% of data set D100. The untrained portion of each data set, 30% of the data, contains 10,000 labels associated with emotional/mental state. P100 is now run on the untrained 30% of data set D100, and P200 is run on the untrained 30% of data set D100. For each model, 10,000 predictions of emotional state of users are generated. For each model, the 10,000 predictions are compared against the 10,000 labels, to see if the predicted emotion (based on the physiological data) matches the actual labelled emotion.

The results in the example are as follows: P100 correctly predicted 6,000 of 10,000 labels in the untrained portion of D100, thus gets a rank of 60%. P200 correctly predicted 8,000 of 10,000 labels in the untrained portion of D100, thus gets a rank of 80%. P200 is chosen as a better-fit, as it has a higher rank.

In a second non-limiting example, matching labels in the assessment phase is not based only on a criterion of "matches/does not match", but allows gradation of matching. In this second example, a prediction by the model of "very happy", when the actual label is "medium happy", gives a score of 75% for that individual match. In this example, for the above models P100, P200 and data set D100, P100 receives an improved rank of 77%, while P200 receives an improved rank of 87%. In this example, P200 is still the better fit prediction model.

In a third non-limiting example, accurate matching of predicted and labelled emotions accounts for 70% of the rank, while performance (speed) accounts for 30%. The lower-accuracy P100 assesses the untrained portion of the data in 5 minutes, and receives a performance grade of 100%. The higher-accuracy P200 assesses the untrained portion of the data in 6 minutes, more slowly than P100, and thus receives a lower performance grade, of 83%. P100 receives an overall grade of 70%*60%+30%*100%=72%. P200 receives an overall grade of 70%*80%+ 30%*83%=80.9%. In this example, P200 is still the higher ranked prediction model. In another example of such a grading, the performance grade could also factor in relative usage of CPU and memory.

It is noted that the methods disclosed with reference to FIG. 4 can be used, in some examples, for training of both association models and prediction models. This may include the use of ranks. These methods can also be used for re-training both association models and prediction models. In some examples, this is done on a periodic basis, and/or in response to arrival of new physiological data and labels of users.

In some examples, system 400 is not capable of training prediction models based on physiological data in database 360 that does not have a sufficient quantity of corresponding labels to enable statistically significant modelling and assessment. In one example, to generate an individual model, 10,000 labels are required. In another example, to generate a physiological data association or prediction model, based on a cluster of 100 users, 50,000 labels are required. In some examples, system 400 is not capable of training association models based on physiological data in database 360 that does not have a sufficient proportion or quantity of corresponding labels. Note that physiological data that does not have corresponding labels can be used, in some examples, by monitoring unit 630 of prediction unit 600, and/or by analytics unit 700. In some examples, physiological data that does not have corresponding labels can also be used by model association unit 610 of prediction unit 600. In some examples, physiological data that does have corresponding labels can be used by model association unit 610, and improve the accuracy of the association.

It should be appreciated that the above module is not bounded by the structure and/or architecture as described with reference to FIG. 4.

Figure 5A:
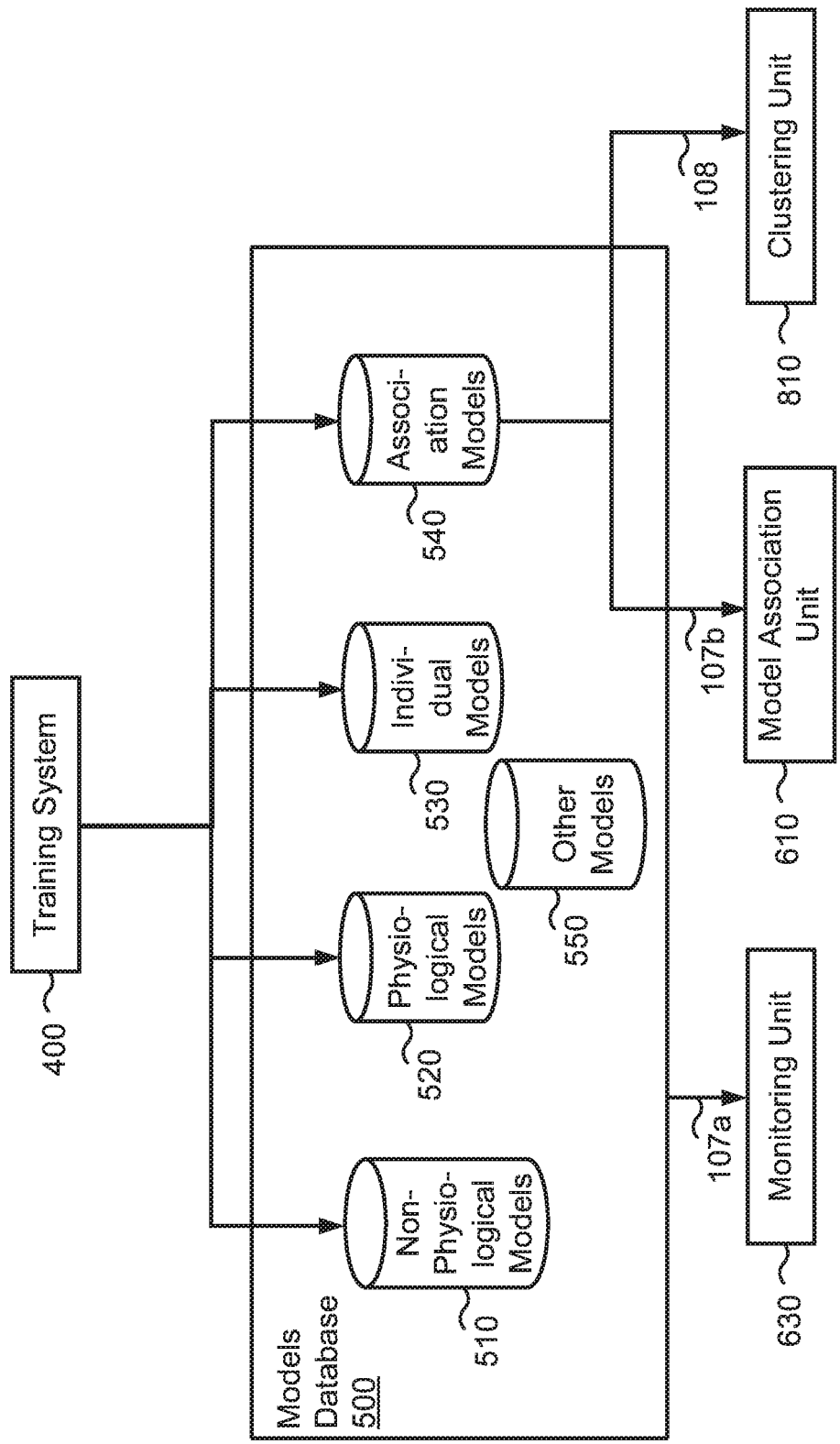
FIG. 5A illustrates a non-limiting generalized scheme example of a models database, in accordance with certain exemplary embodiments of the presently disclosed subject matter.

Turning to FIG. 5A, it illustrates a non-limiting generalized example schematic diagram of the models database 500, in accordance with certain embodiments of the presently disclosed subject matter.

In the models database 500 the system stores, for example, two classes of models which are produced by the training system 400: (a) models which are used to associate users to clusters, e.g. association models 540, and (b) prediction models, which are used for prediction of mental and/or emotional state—e.g. metadata (non-physiological) models 510, physiological models 520, individual models 530 and/or any other models 550.

Figure 7:
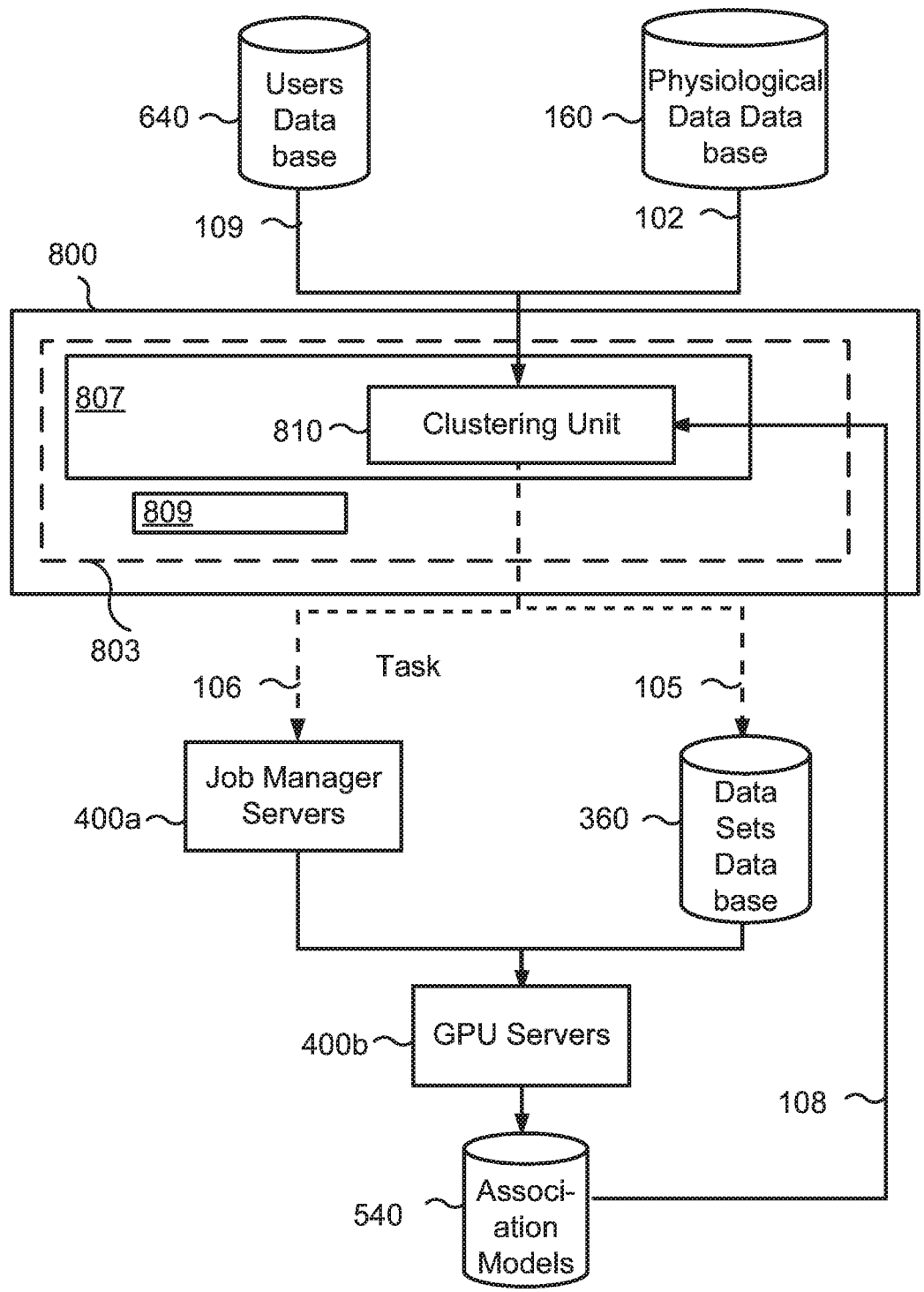
FIG. 7 illustrates a non-limiting generalized flow-chart example of a clustering module, in accordance with certain exemplary embodiments of the presently disclosed subject matter.

In some exemplary embodiments, the association models 540 are created and/or trained (as described above with reference to FIG. 4) based on a cluster dataset (received, for example, from datasets database 360) and on a relevant task (stored e.g. in database 410) which are produced in the clustering system 800, e.g. as described further herein with reference to FIG. 7.

These association models can be used at least (i) for associating individuals to clusters, (i) for the training of the prediction models, and (iii) for associating existing prediction models to new and existing users.

(i) Association models 540 can be used 108 by the clustering unit 810 of system 800, in order to associate individuals to at least two kinds of clusters: (a) non-physiological (e.g., metadata) clusters, used for selecting users (e.g., individuals) for the training of the metadata prediction models, and (b) physiological clusters, used for selecting users (e.g., individuals) for the training of the physiological prediction models, e.g., as described below.

More particularly, for association of users, e.g. individuals, to clusters, at least two types of association models are stored in this component: (1) non-physiological, e.g., metadata) association models (for associating users, e.g., individuals, to non-physiological, e.g., metadata, clusters), (2) physiological association models (for associating users, e.g., individuals, to physiological data clusters), (3) and/or any other association model.

(ii) Training of prediction models is disclosed, for example, with reference to FIG. 7.

(iii) In addition, association models can be used in order to associate a prediction model to a user. In some examples, such an association process can be performed multiple times, from the first entry of a user to the system, and continuously along the user's usage of the system. This association process may be done by model association unit 610 of module 600, which receives 107b association model information from DB 500, based on the ranking of each model with respect to the user.

Regarding the prediction class of models, these models are used for prediction of mental and/or emotional state of a particular user. In some examples the prediction itself is performed by monitoring unit 630 of the prediction module 600 (FIG. 6), that will be addressed further herein with reference to FIG. 6. In some examples, the difference between each prediction model is the cluster of users which were associated together in order to train that model.

In some exemplary embodiments, the first kind of prediction models, non-physiological (e.g., metadata) models 510 may include the models that were trained by system 400 using a dataset which consists of physiological data of multiple individuals that were associated into a cluster according to similarities in their personal (non-physiological) data, for example: age, gender, nationality, and the like. It is noted that in some examples the cluster dataset that is used to train such a model is stored in cluster datasets database 362. The association of users, e.g. individuals, to a cluster can be done by an association model 540, as described below with reference to model association unit 610 in FIG. 6. For example, this kind of model can include multiple models, one or more for each cluster of individuals.

For example, in each kind of model there might be multiple types of models of this kind (for example: in the Metadata Models kind there might be a type of model for men older than 40 years, a type of model for Japanese women, and more).

In some demonstrative embodiments, the second kind of prediction models, physiological models 520 may include the models that were trained by system 400 using a dataset which consists of physiological data of the multiple users that were associated into a cluster according to similarities (e.g., patterns) in their physiological data, for example, heart rate, skin conductivity, body temperature, and the like. It is noted that in some examples the cluster dataset that is used to train such a model is stored in cluster datasets database 362. As one non-limiting example of a cluster based on physiological data, the system may cluster a number of users, who all are characterized in that their skin temperature goes up in the morning, and that their pulse is of approximately a certain value in mid-day. The association of users to a cluster can be done by an association model 540, e.g., as described below with reference to model association unit 610 in FIG. 6. For example, this kind of model can include multiple models, one or more for each cluster of individuals.

For example, in each kind of model there might be multiple types of models of this kind (for example: in the Physiological Models kind there might be a type of model for people who have certain heart rate patterns, people who have certain patterns in skin temperature etc.). In other non-limiting examples, there is one metadata association model and one physiological data association model in association models 540.

In some demonstrative embodiments, the third kind of prediction models, users, e.g., individual, models 530 may include the models that were trained by system 400 using a dataset, which consists of a single individual's physiological data, for example, heart rate, skin conductivity, body temperature, and the like. It is noted that in some examples the user dataset that is used to train such a model is stored in physiological datasets database 361. In some examples, this kind of model can include multiple models, one for each individual.

Note also that in some examples, once a new prediction model is generated (whether an individual model or another type), one or more association models 540 are re-trained, so that they can take into consideration also the newly-generated prediction model.

It is also noted that once an individual model 530 is trained and created, in some examples it can be associated with users other than the single individual whose data was used to train that model. For example, if individual model I250, that was earlier trained based on Karen's physiological data, is later found to be the model with the best fit to Jane's physiological data, Jane can be associated with model I250. In some examples, individual model I250 can then be redefined or re-categorized to be a non-individual physiological model (reference 520), e.g. that is associated with a new cluster that corresponds to similarities in the physiological data of both Jane and Karen. Phrasing it in another way, individual models can in some examples serve as the seeds or bases for other models.

For example, in each kind of model there might be multiple types of models of this kind (for example: in the Individual Models kind there might be a type of model for user a, user b, user c, etc.).

In some demonstrative embodiments, other prediction models 550 may include, for example: (a) models which are trained based on all individuals without associating them to clusters, (b) models that are trained based on a mixture of metadata and physiological data, (c) models that are trained based on a dataset of all users' data and labels that exist in the system (e.g., "global models"), (d) and/or any other models.

Figure 6:
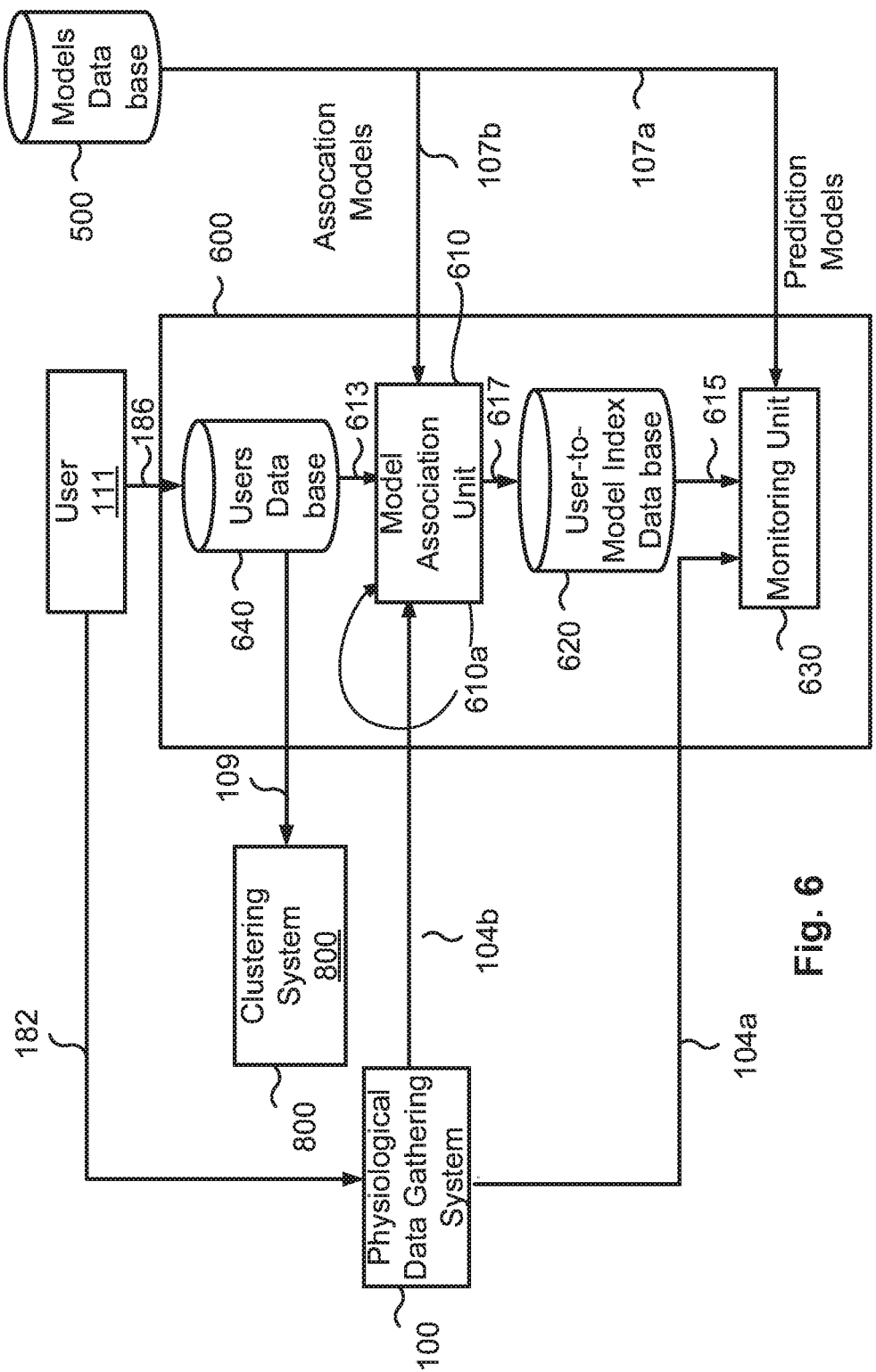
FIG. 6 illustrates a non-limiting generalized flow-chart example of a prediction module, in accordance with certain exemplary embodiments of the presently disclosed subject matter.

For example, some, or all, of the prediction models are used 107*a* by the monitoring unit 630 in order to predict the mental and/or emotional state of the user, for example using methods disclosed herein with reference to FIG. 6.

Figure 5B:
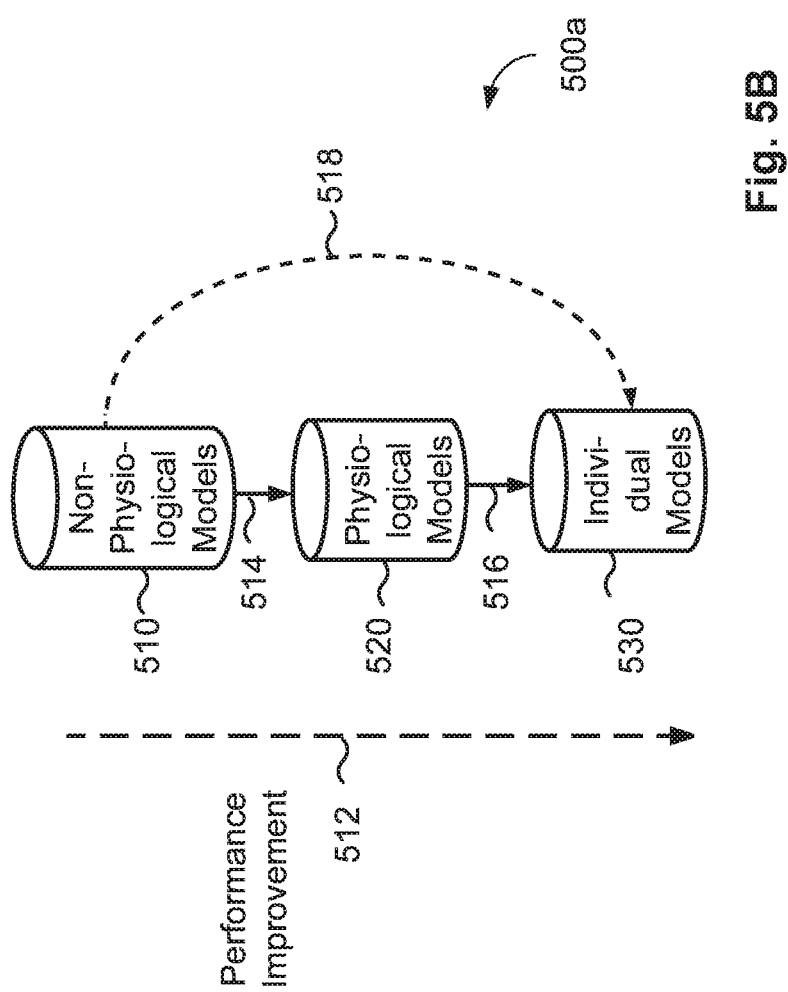
FIG. 5B illustrates anon-limiting generalized example flow chart of model association, in accordance with certain exemplary embodiments of the presently disclosed subject matter.

Turning to FIG. 5B, it illustrates a non-limiting generalized example flow chart of the model association, in accordance with certain embodiments of the presently disclosed subject matter. In some examples, such a flow is performed by model association unit 610 of prediction system 600, as disclosed further herein with reference to FIG. 6. In some demonstrative embodiments, the prediction models flow 500*a* may describe one possible transition between models associated to a particular user. The basic assumption of this method is that there may be, in different time frames, different models which best fit the particular user. The best-fit model for a user may change over time. Therefore, the system may generate multiple kinds of prediction models. The system strives to improve the accuracy of the models, and then associate the most accurate model to each specific user (based for example on the above-mentioned model ranking). Progress and improvement in accuracy may be contingent upon increasing the amount of data for each user, increasing the number of users, and/or increasing the amount of data in general. In some examples, a fit of 60% or more may be a criterion to associate a user to a particular model. In some examples, a fit of 70% or more may be a criterion to associate a user to a particular model.

For the sake of clarity, there follows a simplified non-binding example of the process: a model, which may be associated to a user immediately or almost immediately is, for example, an existing metadata (e.g., non-physiological) model, associated with a particular cluster (e.g., men over age 40). This model in some examples resides in database 510. The required data from the user in order to associate this kind of model to it, is the user's personal information. After a certain period of time (for example, one week of monitoring), in which physiological data were gathered for a user, an existing physiological model, one associated with a particular cluster based on similarities in physiological data, may now be associated 514 with this user. This model in some examples resides in database 520. Usually, the transition 514 of a user to being associated with a physiological model is followed by an improved model predictability and/or prediction performance 512 (for example, determined by the model's ranking). Then, after a longer period of time (for example, 2 weeks), in which additional physiological data of the user were gathered, together with labels that match the physiological data of the user, an individual model may be associated 516 to this particular user. This model in some examples resides in database 530.

It is noted that in some examples, a user can be associated with a non-physiological model, e.g., in 520, based on the user's physiological data only, not accompanied by labels. On the other hand, in some examples in order for the user to be associated with a physiological model, e.g., in 530, the user's physiological data must be accompanied by a sufficient proportion or quantity of labels. In one non-limiting example, the association should utilize at least 1000 labels.

In some demonstrative embodiments, a user that was first associated with a non-physiological, e.g. metadata, model may be associated directly 518 to the individual user model. This scenario is possible in cases where the user does not fit to any existing physiological model in database 520 associated with a cluster, and therefore, this user may be associated with a unique individual model directly.

The above module is not bounded by the structure and/or architecture as described with reference to FIGS. 5A and 5B.

Turning to FIG. 6, it illustrates a non-limiting generalized flow-chart example of the Prediction Module, in accordance with certain embodiments of the presently disclosed subject matter. Prediction module or system 600 may in some examples be a computer. It may, by way of non-limiting example, comprise a processing circuitry (not shown). The processing circuitry may in some examples comprise a processor and a memory (both not shown). Module 600 may also comprise the users database 640 and the user-to-model-index database 620. The processor within system 600 may, in some examples, run at least the model association unit 610 and the monitoring unit 630. In other examples, some or all of the units may be separate hardware units, cloud-based components etc.

In some demonstrative embodiments, when a new or existing user engages with the module (by inputting certain personal information and/or by using the sensing unit 110), it provides 186 the personal information (e.g., non-physiological, metadata) to the users database 640, and provides 182 the physiological data to the physiological data gathering module 100. The users database 640 consists, in some examples, of some or all of a user's personal information. In some examples, database 640 can be referred to herein also as a non-physiological data gathering module, since the non-physiological data is gathered and stored there. In other examples, the non-physiological data module is a system of 198 that receives metadata from e.g. user input via a terminal or the Internet, or from an employer's human resources system. Database 640 in some examples sends 109 this information to the clustering module 800 (e.g. as disclosed further herein with reference to FIG. 7), and also sends it 613 to the model association unit 610, e.g. as described below.

In some examples, the function of the model association unit 610 is to associate a prediction model to any particular user. This prediction model can be a non-physiological, e.g. metadata, model, a physiological model, an individual model and/or any other model. In order to perform this function, the model association unit 610 requests the models database 500 to receive one or more association model(s) 107b. Unit 610 may also obtain 104b physiological data of the particular user from system 100. Unit 610 can use this association model(s) to evaluate and determine which prediction model fits most accurately to a user. In some examples, the association model includes in it information about available prediction models. In some examples, the evaluation is performed also based on the obtained 104b user physiological data. In some examples, the best prediction model for the particular user is an output by the evaluation process. In one non-limiting example, the association model A3 may run user Bill's physiological data against several physiological models: P500 (rank 80), P510 (rank 78), P520 (rank 90), P530 (rank 82). It determines that some of the models, P500 and P520, provide good fits with Bill's data. Since 90 is a higher rank than 80, P520 is chosen to be associated with Bill, and Bill's currently associated model thus has a rank of 90.

In some examples, the most accurate fit between a user and a particular model means that the particular model will deliver the best and most accurate results for the user, in terms of predicting mental and/or emotional states.

For example, it may be that a user has been associated to a cluster utilizing an association model in DB 540. This user may also have been previously associated by unit 610. The model association unit 610 may at a later point in time compare 610a the currently associated prediction model's rank with the rank of other available prediction models in the models database 500. In some examples, this may again be performed by utilizing the association model(s). Thus, if the model association unit 610 found a better performing prediction model in general, and/or for this user, based on the above-mentioned rank, it will associate the higher ranked prediction model to the user. For the sake of clarity, such a process for example, may be performed on each user separately. In some examples this enables or facilitates a customized and/or personalized model-to-user match that will provide the optimal predictability for each user. In some examples, in order to associate a user to a prediction model, there is no need to train using (for example) 70% of the user's physiological data and assess the association using the untrained portion of the physiological data.

In some demonstrative embodiments, the model association unit 610 may be configured to attach to the prediction model a rank of mental state predictability, configured to facilitate prediction of the mental state of the tested user. In one non-limiting example, a user is associated with prediction model P420, with a rank of 80. At a later date, unit 610 uses the association model and new physiological data 104b to perform a new evaluation, and the result is prediction model P440, with a rank of 88.

It is possible that the model association unit 610 will receive 107b multiple association models from models database 500, for example, non-physiological (e.g., metadata) association models, physiological association model and/or any other association models, in order to be able to perform a wide evaluation process. It is also possible that the model association unit 610 will receive 107b only a single association model for the evaluation process. After receiving the association model(s), in some examples the unit 610 then evaluates the best-fit prediction model for the particular user, based on the non-physiological (e.g., metadata) 613 from the users database 640 and/or the physiological data 104b from the physiological data database 160.

The process by which unit obtains 107b models from database 500, so as to perform model association, may in some examples not occur only once per user. In some examples, there is an ongoing process 610a of evaluating and determining which prediction model fits most accurately for a particular user. Ongoing process 610a can in some cases be done periodically, based on certain predetermined and/or manually inputted heuristics, for example, once every day, or after one month of gathering physiological data on a user via interface 104b, and the like.

In some examples, the result of the process performed by model association unit 610 is a prediction model attached to a specific user. In some examples, this output is sent 617 and stored in the user-to-model index database 620. For example, information stored on the user-to-model index database 620 may include user ID, model reference associated with the user (e.g., a path to the prediction model in the models database 500), etc. In some examples, a user record in database 620 also includes the rank determined for the associated prediction model.

In some examples, the next operation performed by prediction system 600, for a particular user, is the prediction of the mental and/or emotional state of the user which is performed in the monitoring unit 630. In order to perform the prediction action, the monitoring unit 630 gets 615 user-to-model information from the user-to-model index database 620, and uses it to request the associated prediction model 107a from the models database 500 (using, for example, the model reference mentioned above). The physiological data of the user may be sent 104a to the monitoring unit 630 from the physiological data gathering module 100. This physiological data is in some cases then used in unit 630 by the prediction model, in order to predict the mental and/or emotional state of the user. For example, the relevant prediction model will be applied to the physiological data. For the sake of clarity, it is possible that the monitoring action will be performed without usage of labels. An example situation of the use of unit 630 is that user Bill already has a prediction model associated with him, and is wearing physiological sensors. New physiological data arrives 182 from these sensors to system 100, and is passed on 104a to unit 640. Unit 630 predicts that at the current time Bill is likely to be in a stressed emotional state.

It is possible that once a certain mental and/or emotional state has been predicted, the monitoring unit 630 may provide some kind of feedback, alert and/or notification to the module 700, and/or, to the user 111 and/or to other software and/or hardware modules. The modules that receive the alert/feedback/notification can be within the system that models emotional/mental state, or be external to it.

The above module is not bounded by the structure and/or architecture as described with reference to FIG. 6.

Turning to FIG. 7, it illustrates a non-limiting generalized flow-chart example of the clustering module 800, in accordance with certain embodiments of the presently disclosed subject matter.

In some demonstrative embodiments, the clustering system or module 800 may include the clustering unit 810, which has two main functions: (a) to orchestrate the creation in datasets database 360 of datasets for the training of the association model(s) and (b) to orchestrate the datasets database 360, in order to produce datasets for training prediction models. In some examples, clustering unit 810 may in some examples be a computer. It may, by way of non-limiting example, comprise a processing circuitry 803. The processing circuitry 803 may in some examples comprise a processor 807 and a memory 809.

In some demonstrative embodiments, clustering module 800 may create datasets for training the association model(s). One input for the clustering unit 810 is the data 109 from the users database 640, which is used in order to create a non-physiological (e.g., metadata) cluster dataset 362, and a matching task in tasks database 410, for the purpose of training a metadata association model, for example according to the methods disclosed with reference to FIG. 4. As one non-limiting example, the clustering unit 810 may identify that certain users have a similar combination of metadata parameters (e.g., female French bank workers over age 40), and unit 810 may instruct 105 to generate a cluster dataset 362 corresponding to them, and to train a metadata association model based on that cluster dataset. For example, the instruction 105 may be sent to processor 307, or to data sets database 360, of pre-processing system 300.

The second input is the physiological data 102 from the physiological data database 160, which in some examples is used in order to create a physiological data cluster dataset 362, and a matching task, for the purpose of training a physiological association model in FIG. 4. As one non-limiting example, the clustering unit 810 may identify that certain users have a similar pattern of increase in blood pressure as a function of time-of-day and day-of-week, and unit 810 may instruct to generate a cluster dataset 362 corresponding to them, and to train a physiological association model based on that cluster dataset.

In some examples, the outputs of this process are a cluster dataset 362 with a matching task that correspondingly serve as inputs for the training module 400 to train association model(s). Training of the association models may make use of physiological data of the users, in the cluster dataset, referred to herein also as second physiological data.

In some demonstrative embodiments, clustering module 800 may orchestrate dataset creation for training of prediction model(s), e.g., 510, 520, 530, 550. One non-limiting example is the orchestration disclosed with reference to FIG. 3A regarding how to create different datasets in database 360 for the purpose of training prediction models. (Datasets are one input of the training module 400). For this function the clustering unit 810 can use 108 the association model(s) 540 from the models database 500 in order to choose relevant users, e.g., individuals, to be put into the cluster, for example, non-physiological, (e.g., metadata) cluster, physiological cluster and/or another cluster, which the prediction model(s) may be based on in its training.

For the sake of clarity there follows a simplified non-binding example of the process: in order to create a non-physiological, e.g. metadata, prediction model for American women under the age of 30, a dataset may be created in the Pre-processing system 300 (FIG. 3A) based on the physiological data of the individuals that exist in the system and match the particular metadata criteria. The clustering unit 810 in this case, will address anon-physiological (e.g., metadata) association model from the association models database 540 of the models database 500 in order to perform evaluation, and unit 810 chooses from all of the users, e.g. individuals, only the ones who match the above criteria. Then, clustering unit 810 instructs the Pre-processing module 300 (FIG. 3A) to create a cluster dataset 362 based on the data and labels of those selected users, e.g. individuals, that match the above criteria. This cluster dataset 362 can then be used as an input for the training process in system 400 of the non-physiological (e.g., metadata) prediction model.

In all of the above scenarios, the clustering system 800 may produce a relevant task 106, which is stored, for example, in database 410. More examples of task generation 106 are disclosed with reference to FIG. 4.

It is noted that in some examples the format of the physiological data in database 160 is more appropriate for use by cluster system 800 than is the physiological data in physiological datasets 361 of dataset database 360.

The above module is not bounded by the structure and/or architecture as described with reference to FIG. 7.

In order to further illustrate some examples of the presently disclosed subject matter, an example of function of the modeling system for a particular user is now disclosed. Bill is registered in the system (for example, by his employer), and his personal information (e.g., age, gender, job, address) are input into users database 640. Database 640 may send 613 this personal information to model association unit 610, or alternatively unit 610 may, for example, periodically query database 640 for users. It may be that unit 610 sees in user-to-model database 620 that no prediction model is associated with Bill. Unit 610 sees that there is no physiological data available yet from physiological data gathering system 100 associated with Bill, which might be used to help associate Bill with a prediction model. Model association unit 610 therefore queries models database 500 for only a metadata association model residing in association models. Unit 610 receives 107b in return metadata association model A1. Unit 610 uses the model A1 to evaluate the prediction models, and chooses model M40 as the best fit. Unit 610 then sends 617 to database 620 a record of data, that contains Bill's ID number in the system and a path in non-physiological models 510 to and metadata prediction model M40. The rank of M40 may also be stored in database 620.

Bill starts wearing one or more body sensors (e.g. measuring heart rate, pulse, skin temperature). His physiological data is sent 186 to physiological data gathering system 100, which stores it in physiological data DB 160, and sends it on 104b to model association unit 610, as well as 104a to monitoring unit 630, and 102 to clustering unit 810. One week later, unit 610 does a periodic evaluation 610a of Bills' model association. It obtains 613 personal information from users database 640, but this time also considers the physiological data 104b. It then queries models database 500 for a metadata association model, as well as for a physiological association model, both residing in association models 540. Unit 610 receives 107b in return metadata association model A1 and physiological association model A3. Unit 610 uses the two association models to evaluate the various prediction models, and finds that model P60 has a higher ranking (e.g., rank 90) than does the previously-associated model M40 (e.g., rank 85). Unit 630 chooses model P60 as the best fit for association to Bill. Unit 610 then sends 617 to database 620 a record of data, that contains Bill's ID number in the system and a path in non-physiological models 510 to physiological prediction model P60. Bill has now been associated with a different model, as disclosed with reference to FIG. 5B.

As indicated above, Bill's physiological data was also sent 104a to monitoring unit 630, from sensing unit 100. In this example, for simplicity of exposition, it is assumed that the evaluation of this physiological data by unit 630 is performed after prediction model P60 has already been associated to Bill. Unit 630 queries user-to-model database 620 with Bill's ID, and receives 615 the response that his associated model is P60 (or receives a path to P60 in queries models database 500). Unit 630 queries database 500 to receive 107a the model P60. Unit 630 runs the prediction model P60 on the newly received 104a physiological data. The resulting prediction is that Bill is mildly depressed, and an alert is sent, for example to a system of Bill's employer.

Two weeks later, Bill participates in an experiment, wherein sensors record his physiological data, while labelling is performed, for example, per method 203 or 205, as disclosed herein with reference to FIG. 2. Again, in a first example of this scenario, Bill's newly acquired physiological data is transferred 182, 104b to model association unit 610. The physiological data is also sent 103 to pre-processing system 300. The labels are stored in labels database 220, and are sent 112 to pre-processing system 300. In some examples, system 300 processes these two inputs 103, 112 and creates a data set DI380, which is stored in data sets database 360. An individual model I280 is created based upon this dataset DI380, as will be exemplified further herein. Note that in some cases the ability to create an individual model is dependent on the availability of a sufficient number of labels in the data set DI380.

Once again, model association unit 610 obtains the physiological data 104b, and it then queries models database 500 for metadata and physiological association models. This time, upon evaluating the various prediction models, unit 610 finds that individual model I280 has a better rank (e.g., 94), than do the various non-individual models evaluated (e.g., 85, 90). Unit 610 then sends 617 to database 620 a record of data, that contains Bill's ID number in the system and a path in individual models 530 to individual prediction model I280. Bill has now been again associated with a different model, as disclosed with reference to FIG. 5B.

In a second example of this scenario, individual model I280 is not created as soon as physiological data 103 and corresponding labels 112 are available. In this second example, model association unit 610 evaluates the various prediction models, utilizing the association models received 107b. If and when unit 610 finds that none of the non-individual prediction models (metadata models or physiological models) fit in a sufficiently good respect to Bill's physiological data (including the newly acquired data), that is, none of them have a rank above at least a threshold (e.g., 65%), only then (in this second example) is the individual model I280 generated. In this example, unit 810 detects that the fit of Bill's model is not sufficiently good, and orchestrates the generation of Bill's individual model I280 based on data set DI380, as will be exemplified further herein. In one example, unit 810 is in connection (not shown in the figures) with user-to-model index data based 620, and identifies users whose associated prediction models are of a relatively low rank.

Looking now at some examples of model training and generation, upon registration in the system, Bill's personal info (e.g., metadata) is in some examples also sent 109 from users database 640 to clustering unit 810 of clustering system 800. In some examples, clustering unit 810 decides, based on the metadata of Bill and possibly additional new registrants, to create new metadata cluster(s). Unit 810 uses a metadata association model 108 from association models 540 to choose the users who will be members of the metadata cluster(s). The cluster dataset will have data of certain users selected by unit 810. Unit 810 may then request 105 that the data set database 360 create or generate one or more new metadata cluster datasets in 362, for the new metadata clusters. Unit 810 may then send 106 one or more tasks to be stored in tasks database 410, for training system 400 to train one or more new metadata prediction models, based on the task(s) and based on the newly created metadata cluster dataset(s) 113. The new trained metadata prediction models are then stored by system 400 in non-physiological models 510 within models database 500.

In other examples, clustering unit 810 can in some cases choose to use the metadata of Bill and other new registrants to re-train existing metadata prediction models residing in non-physiological models 510 (e.g., existing metadata models that correspond to Bill's gender, age and/or job and the like), rather than to train new models.

Bill's physiological data may be monitored, for example, using body sensors. In some examples it is passed 182, 102 to clustering unit 810 via the physiological data database 160 of physiological data gathering system 100. The clustering unit 810 decides, based on the physiological data of Bill and possibly additional users, to create new physiological data cluster(s), based on certain similarities between the physiological data of these users. Unit 810 uses a physiological data association model 108 from association models 540 to choose the users who will be members of the physiological data cluster(s). The cluster dataset will have data of certain users selected by unit 810. Unit 810 may then request 105 that the data set database 360 create one or more new physiological data cluster datasets in 362, for the new physiological data clusters. Unit 810 may then send 106 one or more tasks to be stored in tasks database 410, for training system 400 to train one or more new physiological data prediction models, based on the task(s) and based on the newly created physiological data cluster dataset(s) 113. The new trained physiological data prediction models are then stored by system 400 in physiological models 520 within models database 500.

In other examples, clustering unit 810 can in some cases choose to use the physiological data of Bill and other users to re-train existing physiological data prediction models residing in physiological models 520, rather than to train new models.

Regarding the example generation of individual model I280 associated with Bill, disclosed above, the process may in some examples be as follows. In a first example of this scenario, clustering unit decides to create an individual model corresponding to Bill. For example, it may notice that physiological data 102 of Bill has been received, but that no individual model has yet been generated for Bill. In a second example of this scenario, clustering unit 810 receives a request from model association unit 610 to create an individual prediction model corresponding to Bill. As has been outlined above, in some examples a data set DI380 corresponding to this physiological data 102 of Bill's has been generated and stored in data sets database 360, for example in physiological datasets 361. Unit 810 may then send 106 one or more tasks to be stored in tasks database 410, for training system 400 to train one or more new physiological data prediction models, based on the task(s) and based on the newly created dataset DI380, and possibly earlier datasets containing Bill's physiological data. The new trained individual prediction model I280 is then stored by system 400 in individual models 530 within models database 500. Note that in some cases the ability to create an individual model is dependent on the availability of a sufficient number of labels in the data set DI380. It is noted also that in some examples, the generation of the new model I280 may cause modification of one or more association models, such that they will consider I280 as one of the possible prediction models to which users may be associated.

In other examples, clustering unit 810 can in some cases choose to use the newer physiological data of Bill, to re-train the existing individual prediction models I280 corresponding to Bill, which is residing in individual models 530, rather than to train a new individual model corresponding to Bill.

In some examples, the clustering unit's 800 receiving of Bill's metadata 109 from user database 640 can trigger orchestration by unit 800 of generation of a new metadata association model. In some examples, the clustering unit's 800 receiving of Bill's physiological data 102 from physiological data database 160 can trigger orchestration by unit 800 of generation of a new physiological association model. Unit 800 may instruct 105 the data sets database 360 to generate a new cluster dataset, based on clusters of users chosen for their similarities in metadata, or in physiological data, as may be relevant. Unit 800 may then send a task 106 to training system 400, to use this generated cluster dataset data 113 in sets database 360 to train a new metadata association model 540 or physiological association model 540, as may be relevant.

In other examples, clustering unit 810 can in some cases choose to use the metadata 109 of Bill, and/or the physiological data 102 of Bill, to re-train existing metadata association models 540 or physiological association models 540, as may be relevant, rather than to train a new association model corresponding to Bill.

Figure 8A:
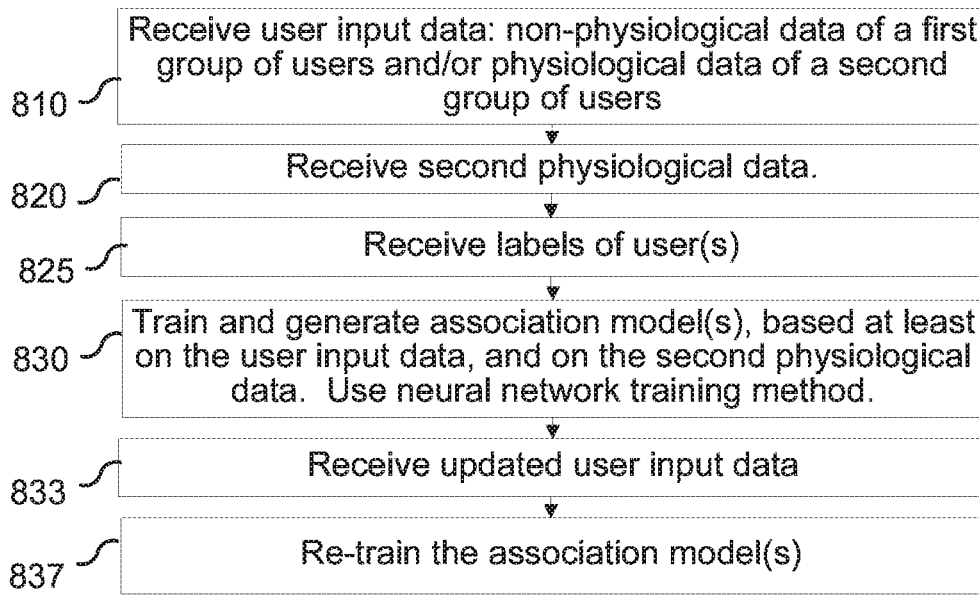
FIG. 8A illustrates a non-limiting generalized flow-chart example of modeling, in accordance with certain exemplary embodiments of the presently disclosed subject matter.

Turning now to FIG. 8A, it illustrates a generalized flow chart of modeling, in accordance with certain exemplary embodiments of the presently disclosed subject matter. Method 800 is an example method for training and generating association models. In some examples, this can be performed by the processing circuitry 407 of training system 400.

According to some examples, training system 400 receives non-physiological data of a first group of users and/or physiological data of a second group of users (block 810). The non-physiological data and/or physiological data constitute user input data. In some examples, the user input data includes data of a plurality of users, and the user input data of the multiple users share similarities.

According to some examples, training system 400 receives second physiological data (block 820).

According to some examples, training system 400 receives labels of users (block 825).

According to some examples, training system 400 trains, and generates, one or more association models, based at least on the user input data (block 830). The training is in some examples based also on the second physiological data. The training is in some examples based also at least partly on the labels. In some examples, generation of the association model(s) is based at least partly on the physiological data of the user input data. In some examples, generation of the association model(s) is based at least partly on the similarities of physiological data of users. In some examples, generation of the association model(s) is based at least partly on non-physiological data of the user input data. In some examples, the training of the association model(s) is done according to a neural network training method.

According to some examples, training system 400 receives updated user input data (block 833). This updated user input data includes, in some examples, updated non-physiological data of a first group of users, and/or updated physiological data of a second group of users.

According to some examples, training system 400 re-trains one or more of the association models, in response to receiving the updated user input data (block 835). This updated user input data includes, in some examples, updated non-physiological data of a first group of users, and/or updated physiological data of a second group of users. This may, for example, include performing blocks 825 to 830 again, while considering the updated user input data as part of the user input data to the training process. Note that the steps 833 and 835 may be performed in an ongoing fashion.

Figure 8B:
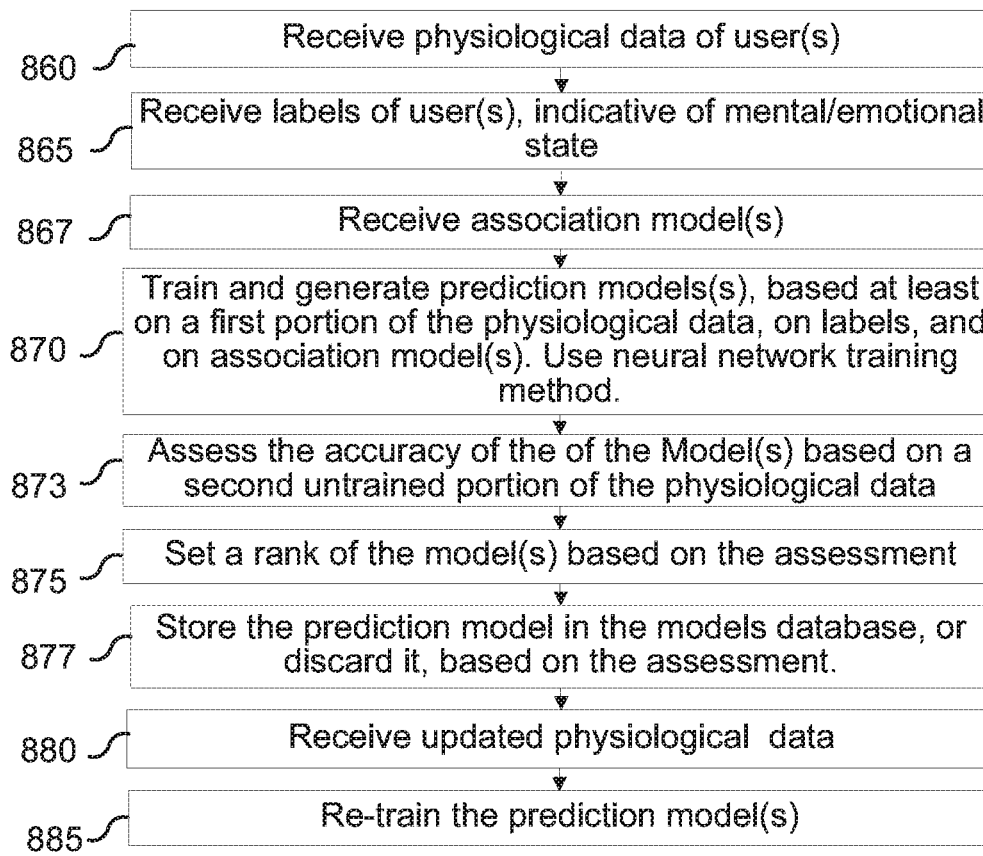
FIG. 8B illustrates a non-limiting generalized flow-chart example of modeling, in accordance with certain exemplary embodiments of the presently disclosed subject matter.

Turning now to FIG. 8B, it illustrates a generalized flow chart of modeling, in accordance with certain exemplary embodiments of the presently disclosed subject matter. Method 850 is an example method for training and generating prediction models. In some examples, this can be performed by the processing circuitry 407 of training system 400.

According to some examples, training system 400 receives physiological data of one or more users (block 860). In some examples, the physiological data includes data of a plurality of users, and the physiological data of the multiple users share similarities, for example similarities in physiological patterns.

According to some examples, training system 400 receives labels of user(s), corresponding to at least a portion of the physiological data of the user(s) (block 865).

According to some examples, training system 400 receives one or more association models (block 867).

According to some examples, training system 400 trains, and generates, one or more prediction models, based at least on the physiological data (block 870). The training is in some examples based also at least partly on the labels. In some examples, generation of the prediction model(s) utilizes one or more association models. In some examples, generation of the association model(s) is based at least partly on the similarities of physiological data of users. In some examples, the training of the association model(s) is done according to a neural network training method. In some examples, training is done on a first portion of the received physiological data.

According to some examples, training system 400 assesses the accuracy of the trained prediction model(s), based on a second, untrained, portion of the received physiological data (block 873).

According to some examples, training system 400 sets ranks of the prediction model(s) based on the assessments (block 875).

According to some examples, training system 400 stores the prediction model(s) in the models database, based on the results of the assessment (block 877). In some examples, if a model does not receive a sufficiently high rank, it is not stored.

According to some examples, training system 400 receives updated physiological data (block 880).

According to some examples, training system 400 re-trains one or more of the association models, in response to receiving the updated physiological data (block 885). This may, for example, include performing blocks 865 to 877 again, while considering the updated user input data as part of the user input data to the training process. It is noted that steps 880 and 885 may be performed in an ongoing fashion.

Figure 9:
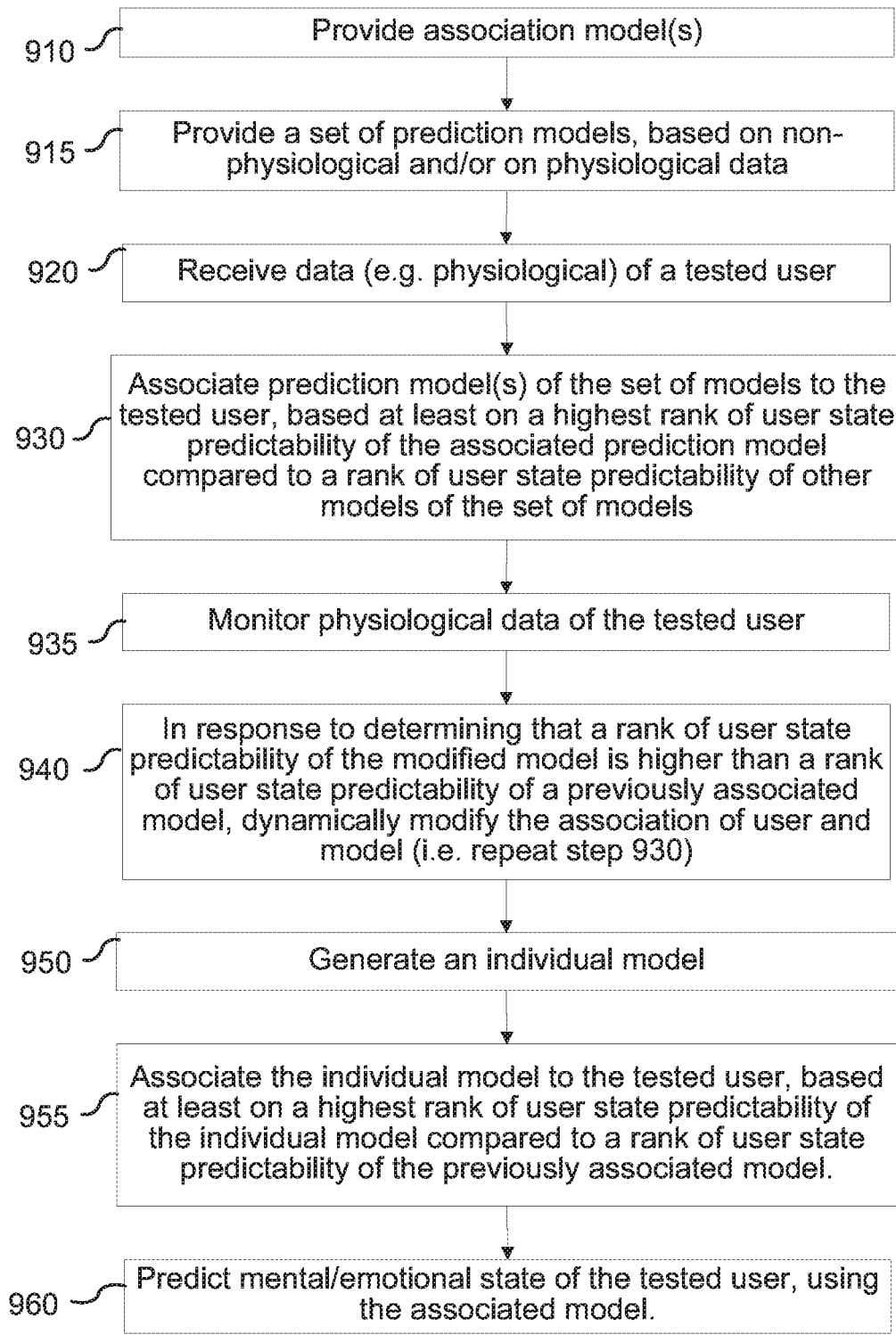
FIG. 9 illustrates a non-limiting generalized flow-chart of association and prediction, in accordance with certain exemplary embodiments of the presently disclosed subject matter.

Turning now to FIG. 9, it illustrates a generalized flow chart of association and prediction, in accordance with certain exemplary embodiments of the presently disclosed subject matter. In some examples, method 900 can be performed by the processing circuitry of prediction system 600, for example by model association unit 610 and monitoring unit 630.

According to some examples, one or more association models are provided to system 600 (block 910).

According to some examples, one or more prediction models are provided to system 600 (block 915). The prediction models in some cases facilitate prediction of a mental and/or emotional state of a user. They may be referred to herein as a set of models. The set of prediction model(s) received or provided includes one or more first model(s) based on non-physiological data gathered from a first group of users, and/or one or more second models based on physiological data gathered from a second group of users.

According to some examples, data of a tested user are provided to system 600 (block 920). In some examples, this received or provided data of a tested user includes physiological data. In some examples, the provided data of the tested user also includes label data corresponding to at least a portion of the physiological data.

According to some examples, at least one model of the set of models is associated to the tested user (block 930). This model may be referred to herein as an associated prediction model. The association in some examples is based at least on a highest rank of user state predictability of the associated prediction model compared to a rank of user state predictability of other models within the set of models. In some examples, the association is based at least partly on at least one association model. In some examples, the highest rank of user state predictability of the associated model and the rank of user state predictability of other models are determined at least based on the physiological data gathered from the first group of users and from the second group of users. In some examples, the highest rank of user state predictability of the associated prediction model and the rank of user state predictability of other models are indicative of at the mental/emotional state of the tested user.

According to some examples, physiological data of the tested user is monitored (block 935).

According to some examples, in response to determining that the rank of user mental state predictability of another prediction model is higher than the rank of user state predictability of the associated prediction model, the prediction model associated with the user is dynamically modified (block 940). In some examples, the determination of the higher rank of the other model is based at least partly on the monitoring of physiological data of the tested user in block 935. In some examples, this block includes a repetition of block 930. This other prediction model is set to constitute the associated prediction model. It is noted that the steps 935 and 940 may be performed in an ongoing fashion.

According to some examples, an individual model is generated (block 950). This block is performed, in some examples, by modelling system or module 900.

According to some examples, the individual model is associated to the tested user (block 955). In some examples, this is done based at least on a highest rank of user state predictability of the individual model compared to a rank of user state predictability of the previously associated prediction model. In some examples, blocks 950 and 955 are performed, based at least on the rank of user state predictability of the models of the set of models not meeting a threshold. In a non-limiting example, this threshold is 65 percent.

According to some examples, the mental state and/or the emotional state of the tested user are predicted, using the associated model user (block 955). In some examples, monitored physiological data is utilized as an input for this prediction. In some examples, blocks 910 to 940, and 955 are performed by model association unit 610. In some examples, blocks 960 are performed by monitoring unit 630.

Figure 10:
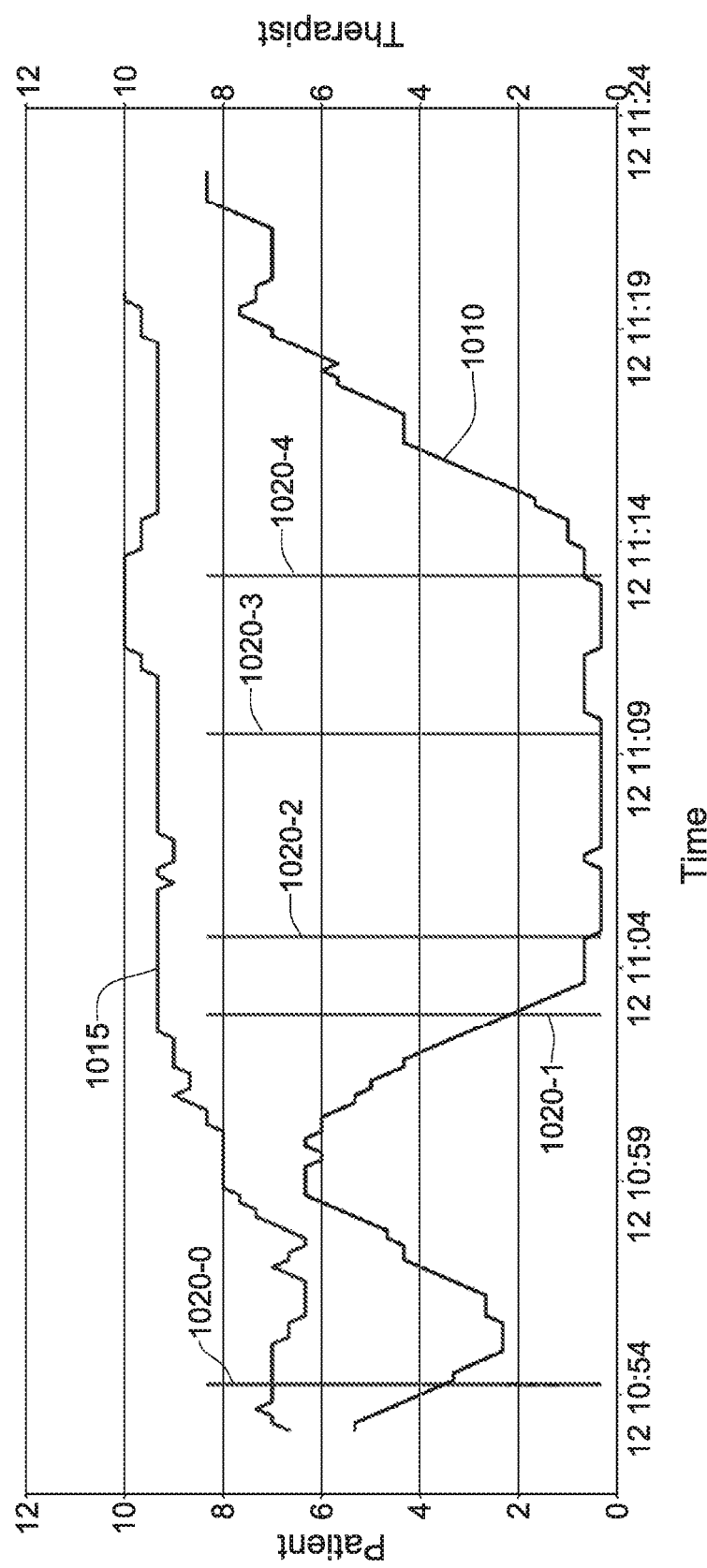
FIG. 10 illustrates an example graph of prediction of an emotional/mental state, in accordance with certain exemplary exemplary embodiments of the presently disclosed subject matter.

Turning now to FIG. 10, it illustrates an example graph of prediction of an emotional/mental state, in accordance with certain exemplary embodiments of the presently disclosed subject matter. Graph 1005 illustrates a non-limiting actual use of a prediction model in predicting an emotional/mental state of a user. The scenario is an actual clinical psychotherapeutic session involving a patient and a psychiatrist. The X-axis indicates that the session took place over 30 minutes, between 10:54 and 11:24 on the 12th of the month. The psychotherapy session of the example used the Imagery Rescripting (IR) technique. In some examples of this technique, the first stage is Beginning, having a relaxing discussion of the Recent Situation 1020-0, during which the patient not in an overly stressful or emotionally loaded situation (possibly after some initial time adjusting to the situation of the session). The session then progresses to three stages, Float Back 1020-1, Historic Situation 1020-1, and Imagery Rescripting 1020-3, that are expected, in many cases, to cause a high emotional load on the patient and be stressful to him or her. The final stage is ending the IR, and having a relaxing post-session talk 1020-4, during which the emotional load on the patient is expected to decrease, until reaching a normal level. The references 1020-0 through 1020-4 indicate where each stage of discussion began, in the example actual session.

During the session, both the patient and the therapist were connected to sensors or other devices that captured at least the following physiological data 182: Photoplethysmogram (PPG) measuring heart rate; Electrodermal activity (EDA) sensor, measuring skin conductivity; skin temperature; and an accelerometer on a wrist band, sensing body motion. The physiological data was fed into a system 198 of modelling human emotional state and/or mental state, which applied, to both participants, a (non-individual) physiological prediction model 520. The system did not know about the occurrence of the psychotherapy session, nor of its time of occurrence, nor of the timing of the five stages. As the session progressed, the monitoring unit 630 predicted levels of emotional load and stress, based on the continually incoming physiological data 182, for both the patient 1010 and the therapist 1015. As seen on the Y-axis of the graph, the measure for emotional load used in the example assigns a score of 0 to a high emotional load (e.g., stressed) and a score of 10 to a low emotional load (e.g., relaxed).

Looking at the results of the prediction, it can be seen on plot 1010 that the patient was in various levels of relaxation early in the session, became very stressed at the times corresponding to stages 1020-1 through 1020-3, and during 1020-4 gradually returned to a normal level of stress and emotional load. These levels of stress predicted by the system, based on physiological data and a physiological prediction model, without knowledge of the therapy session, correspond well to the therapy dynamics, that is to the stress levels expected for each stage of the IR technique according to the therapy protocol.

Plot 1015 acts as a control on the data of plot 1010. Plot 1015 shows that unit 630 predicted comparatively low levels of stress for the therapist throughout the session. This corresponds well to the fact that the IR technique is not intended to induce emotional load on the therapist, but only on the patient.

Only certain components are shown, as needed to exemplify the presently disclosed subject matter. Other components and sub-components, not shown, may exist. Systems such as those described with respect to the non-limiting examples of FIGS. 1A through 7 may be capable of performing all, some, or parts of the methods disclosed herein.

Any or all of the processing circuitries disclosed above may be, in non-limiting examples, a general-purpose computer specially configured for the desired purpose by a computer program stored in a non-transitory computer-readable storage medium. It may be configured to execute several functional modules in accordance with computer-readable instructions.

Each system component and module in FIGS. 1A through 7 can be made up of any combination of software, hardware and/or firmware, executed on a suitable device or devices, that perform the functions as defined and explained herein. Equivalent and/or modified functionality, as described with respect to each system component and module, can be consolidated or divided in another manner. Thus, in some embodiments of the presently disclosed subject matter, the system may include fewer, more, modified and/or different components, modules and functions than those shown in FIGS. 1A through 7. To provide one non-limiting example of this, in FIG. 3A one processor 307 is shown, performing several steps of a process. In other examples, one or more of these steps could each be performed on separate processors, in some examples located in different locations. Similarly, in the example of FIG. 6, one processor (not shown) runs the functions of units 610 and 630 and in the example of FIG. 1C, one processor 124 runs the functions of units 110 through 150. In other examples, each of those units could each be separate processors, or even completely separate computers in separate servers or racks, in some examples located in different locations.

Similarly, in the example of FIGS. 1A to 7, each of the systems 100, 200, 300, 400, 800, 600, 700, is disclosed as comprising its own processor (e.g. 123, 214, 307, 407, 807) and memory (e.g. 123, 216, 309, 409, 809). In some other examples, one or more of the systems 100, 200, 900, 600, 700, disclosed with reference to FIG. 1A, can be separate software modules running on the same processor, and in some cases sharing the same memories.

It is also noted that each processing circuitry disclosed herein has been described as comprising a memory. In some examples, these memories hold data used in a transitory manner during the performance of various calculations. It is further noted that a number of systems have been disclosed as including databases supporting various functionalities, for example the databases 160, 220, 360, 410, 500, 620, and 640, and databases 360 and 500 are disclosed in FIGS. 3B and 5B as including several databases. In other examples, some or all of these databases can be combined, or their contents divided differently than as described, and some may be located external to some or all of the relevant systems (e.g. 100, 200, 300, 400, 600) but operatively coupled to them. Yet further, it is noted that all of the databases disclosed herein are non-limiting examples of data stores residing in a storage. In other examples, there may be different divisions of storage between the memories and other storage such as the databases disclosed. As one non-limiting example, in some cases users database 640 may not be part of the prediction system 600, but rather separate from it.

Each component in FIGS. 1A through 7 may represent a plurality of the particular component, possibly in a distributed architecture, which are adapted to independently and/or cooperatively operate to process various data and electrical inputs, and for enabling operations related to modelling and prediction of mental and/or emotional states. In some cases multiple instances of a component may be utilized for reasons of performance, redundancy and/or availability. Similarly, in some cases, multiple instances of a component may be utilized for reasons of functionality or application. For example, different portions of the particular functionality may be placed in different instances of the component. One or more of these components and modules can be centralized in one location, or dispersed and distributed over more than one location.

FIGS. 1A through 7 illustrate only a general schematic of the system architecture and data flows, describing, by way of non-limiting example, one aspect of the presently disclosed subject matter in an informative manner only, for clarity of explanation only. It will be understood that that the teachings of the presently disclosed subject matter are not bound by what is described with reference to FIGS. 1A through 7.

In some embodiments, one or more steps of the various flows exemplified herein may be performed automatically.

It is noted that the teachings of the presently disclosed subject matter are not bound by the flow charts and architectures illustrated in the various figures. The operations can occur out of the illustrated order. Similarly, some of the operations or steps can be integrated into a consolidated operation or can be broken down to several operations, and/or other operations may be added. It is also noted that whilst the flow charts are described with reference to system elements that realize them, such as for example processing circuitries 122, 303 and others, this is by no means binding, and the operations can be performed by elements other than those described herein.

In exemplary embodiments of the presently disclosed subject matter, fewer, more and/or different stages than those shown in the figures can be executed. In exemplary embodiments of the presently disclosed subject matter one or more stages illustrated in the figures can be executed in a different order and/or one or more groups of stages may be executed simultaneously as should be appreciated to those skilled in the art.

It is to be understood that the methods and systems described above are not limited in its application to the details set forth in the description contained herein or illustrated in the drawings. The methods and systems are capable of other embodiments and of being practiced and carried out in various ways. While there has been shown and disclosed examples in accordance with the presently disclosed subject matter, it will be appreciated that many changes may be made therein without departing from the spirit of the presently disclosed subject matter. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the presently disclosed subject matter.

It will also be understood that the system according to the demonstrative embodiments described above may be, at least partly, implemented on a suitably programmed computer. Likewise, the demonstrative embodiments may contemplate a computer program product being readable by a computer for executing the method of the invention. The demonstrative embodiments further contemplate a non-transitory machine-readable or computer-readable memory tangibly embodying a program of instructions executable by the machine or computer for executing the one or more methods which may be implemented by some demonstrative embodiments, or any part thereof as described above. The presently disclosed subject matter further contemplates a non-transitory computer readable storage medium having a computer readable program code embodied therein, configured to be executed so as to perform the method of the presently disclosed subject matter.

What is claimed:

1. A computer-controlled system for modeling a state of a user, the system comprising:
a processing circuitry configured to:
generate a plurality of prediction models for predicting at least one of a mental state of a user and an emotional state of the user, wherein the plurality of prediction models comprises at least one of at least one first model based on non-physiological data of a first group of users and at least one second model based on physiological data of a second group of users, such that the plurality of prediction models form a set of models;
receive data of a tested user;
associate at least one model of the set of models to the tested user to form an associated prediction model that is based at least on the received data of the tested user and on a highest rank of a user state predictability of the associated prediction model compared to a rank of a user state predictability of other models of the set of models;
dynamically repeat the forming of the associated prediction model in response to determining that a rank of user state predictability of another prediction model of the set of models is higher than a rank of user state predictability of the associated prediction model; and
set the another prediction model as a current associated prediction model, such that the current associated prediction model is configured to be used to predict at least one of a mental state of the tested user and an emotional state of the tested user.

2. The system of claim 1, wherein the received data of the tested user comprises physiological data.

3. The system of claim 2, wherein the received data of the tested user further comprises label data corresponding to at least a portion of the physiological data.

4. The system of claim 2, wherein the processing circuitry is configured to determine a highest rank of the user state predictability of the associated at least one model and the rank of user state predictability of other models at least based on the physiological data gathered from the first group of users and from the second group of users.

5. The system of claim 4, wherein the highest rank of user state predictability of the associated prediction model and the rank of user state predictability of other models is indicative of at least one of the mental state of the tested user and the emotional state of the tested user.

6. The system of claim 1, wherein the association of the at least one model of the set of models to the tested user is based at least partly on at least one association model.

7. The system of claim 1, wherein the processing circuitry is configured to determine that the rank of the user state predictability of the another prediction model is higher than the rank of user state predictability of the previously associated model based at least partly on monitoring of physiological data of the tested user.

8. The system of claim 4, wherein the processing circuitry is further configured to:
generate an individual model; and
associate the individual model to the tested user based at least on the received data of the tested user and on the highest rank of user state predictability of the individual model compared to a rank of user state predictability of the associated prediction model.

9. The system of claim 8, wherein the processing circuitry is further configured to generate the individual model and to associate the individual model based at least on the rank of user state predictability of the models of the set of models that do not meet a threshold.

10. The system of claim 9, wherein the threshold is 65 percent.

11. The system of claim 1, wherein the processing circuitry is further configured to use the associated model to predict the at least one of the mental state of the tested user and the emotional state of the tested user.

12. The system of claim 1, wherein the physiological data comprise at least one of heart rate, skin conductivity, body temperature, pulse, blood perfusion and blood flow.

13. A non-transitory computer readable storage medium tangibly embodying a program of instructions that, when executed by processing circuitry of a computer, causes the computer to:
generate a plurality of prediction models for predicting at least one of a mental state of a user and an emotional state of the user, wherein the plurality of prediction models comprises at least one of at least one first model based on non-physiological data of a first group of users and at least one second model based on physiological data of a second group of users, such that the plurality of prediction models form a set of models;
receive data of a tested user;
associate at least one model of the set of models to the tested user to form an associated prediction model that is based at least on the received data of the tested user and on a highest rank of a user state predictability of the associated prediction model compared to a rank of a user state predictability of other models of the set of models;

dynamically repeat the forming of the associated prediction model in response to determining that a rank of user state predictability of another prediction model of the set of models is higher than a rank of user state predictability of the associated prediction model; and set the another prediction model as a current associated prediction model, such that the current associated prediction model is configured to be used to predict at least one of a mental state of the tested user and an emotional state of the tested user.

14. A computer-implemented method for modeling a state of a user, the method comprising:

generating a plurality of prediction models for predicting at least one of a mental state of a user and an emotional state of the user, wherein the plurality of prediction models comprises at least one of at least one first model based on non-physiological data gathered from a first group of users and at least one second model based on physiological data gathered from a second group of users, such that the a plurality of prediction models forming a set of models;

receiving data of a tested user;

associating at least one model of the set of models to the tested user to form an associated prediction model that is based at least on the received data of the tested user and on a highest rank of a user state predictability of the associated prediction model compared to a rank of user state predictability of other models of the set of models;

dynamically repeating the forming of the associated prediction model in response to determining that a rank of the user state predictability of another prediction model is higher than a rank of the user state predictability of the associated prediction model; and setting the another prediction model as a current associated prediction model, such that the current associated prediction model is configured to be used to predict at least one of a mental state of the tested user and an emotional state of the tested user.

15. A computer controlled system for modeling a state of a user, the system comprising:

a physiological data gathering module configured to gather physiological data of a user according to one or more physiological measurements of the user acquired over a time frame;

a non-physiological data gathering module configured to gather non-physiological data of a user;

a labelling module configured to provide one or more labels indicative of at least one of a mental state and an emotional state of the user at a time mark in the time frame based on at least one of the non-physiological data of the user and the physiological data of the user; and a modelling module configured to generate a plurality of models for predicting at least one of the mental state and the emotional state of the user, such that the plurality of prediction models form a set of models, wherein the plurality of prediction models comprises at least one of a first model based on non-physiological data gathered from a first group of users, a second model based on the one or more labels and the physiological data gathered from a second group of users, and a third model including an individual model configured to predict the mental state or the emotional state of an individual user, wherein each one of the first model, the second model and the third model is associated with a rank of a user state predictability configured to facilitate prediction of at least one of a mental state and an emotional state of a tested user, and wherein the modelling module is further configured to:

associate at least one model of the set of models to the tested user to form an associated prediction model that is based at least on received data of the tested user and on a highest rank of a user state predictability of the associated prediction model compared to a rank of user state predictability of other models of the set of models;

dynamically repeat the forming of the associated prediction model in response to determining that a rank of the user state predictability of another prediction model is higher than a rank of user state predictability of the associated prediction model; and set the another prediction model as a current associated prediction model, such that the current associated prediction model is configured to be used to predict at least one of a mental state of the tested user and an emotional state of the tested user.

16. The system of claim 15, wherein the rank of the user mental state predictability is determined according to the physiological data of the tested user that is gathered over the time frame.

17. The system of claim 16, wherein, for a model of the first, second and third models, the modelling module is configured to predict the mental state of the tested user based on at least a portion of the gathered data and compare the predicted mental state with a corresponding mental state as indicated by a label of the labels and determine the rank associated with the model according to one or more performance metrics of the comparison.

18. The system of claim 17, wherein the modelling module is configured to associate the tested user with the model of the first, second and third models having the highest rank of the user mental state predictability.

19. The system of claim 15, wherein the first model and the second model are arranged in one or more clusters that each comprise at least two users having at least one of common physiological data and common non-physiological data.

20. The system of claim 15, further comprising a prediction module configured to predict the mental state of the tested user based on at least one of the first model the second model and the third model, without utilizing the mental state data indicated by the labels.

21. The system of claim 20, wherein the prediction module is configured to predict the mental state of the user by applying the first model to the non-physiological data of the tested user.

22. The system of claim 20, wherein the prediction module is configured to predict the mental state of the user by applying the second model to the user physiological data.

23. The system of claim 20, wherein the prediction module is configured to predict the mental state of the user by applying the third model to the physiological data of the tested user.

24. The system of claim 20, wherein the prediction module is configured to receive at least a portion of the physiological data of the tested user and predict the mental state of the tested user based on at least one of the first model, the second model and the third model.

25. The system of claim 20, further comprising an analytic unit configured to receive from the prediction module data related to a predicted mental state of one or more users and to generate aggregated business insights of the one or more users.

26. The system of claim 15, wherein the modelling module comprises a pre-processing module configured to generate a dataset based on the one or more labels from the labelling module and the physiological data.

27. The system of claim 26, wherein the modelling module further comprises a clustering module configured to instruct the pre-processing module to generate the dataset based on at least one of a selected physiological data of the physiological data and a selected label of the one or more labels.

28. The system of claim 27, wherein the modelling module further comprises a training module configured to generate the second model by training the generated dataset according to a training task from the clustering module.

29. The system of claim 28, wherein the training module comprises at least one graphic processing units configured to train the dataset and the third model according to a neural network training method.

30. The system of claim 29, further comprising a models database configured to receive one of the second model and the third model from the GPU and configured to use the neural network training method to set the rank by training a first portion of the dataset, assess an accuracy of the second model based on a second untrained portion of the dataset, and store the second model in the models database based on the assessment.

* * * * *